(12) United States Patent
Cipolla

(10) Patent No.: US 9,393,288 B2
(45) Date of Patent: Jul. 19, 2016

(54) METHODS OF TREATING DISEASES ASSOCIATED WITH PPARγ

(71) Applicant: The University of Vermont and State Agricultural College, Burlington, VT (US)

(72) Inventor: Marilyn J. Cipolla, Colchester, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 13/795,685

(22) Filed: Mar. 12, 2013

(65) Prior Publication Data
US 2013/0324468 A1 Dec. 5, 2013

Related U.S. Application Data

(60) Provisional application No. 61/652,406, filed on May 29, 2012.

(51) Int. Cl.
| | | |
|---|---|---|
| *A61K 38/22* | (2006.01) | |
| *A61P 5/02* | (2006.01) | |
| *A61P 25/00* | (2006.01) | |
| *A61P 9/00* | (2006.01) | |
| *A61K 45/06* | (2006.01) | |
| *A61K 31/425* | (2006.01) | |

(52) U.S. Cl.
CPC ........... *A61K 38/2221* (2013.01); *A61K 31/425* (2013.01); *A61K 45/06* (2013.01)

(58) Field of Classification Search
None
See application file for complete search history.

(56) References Cited

U.S. PATENT DOCUMENTS

| | | |
|---|---|---|
| 5,759,807 A | 6/1998 | Breece et al. |
| 5,811,395 A | 9/1998 | Schwabe et al. |
| 5,945,402 A | 8/1999 | Cipolla et al. |
| 6,200,953 B1 | 3/2001 | Schwabe et al. |
| 6,251,863 B1 * | 6/2001 | Yue ................. 514/9.7 |
| 6,723,702 B2 | 4/2004 | Conrad et al. |
| 2003/0158376 A1 | 8/2003 | Schwabe et al. |
| 2004/0122059 A1 * | 6/2004 | Cantorna et al. ......... 514/342 |
| 2011/0130332 A1 | 6/2011 | Park et al. |
| 2011/0137291 A1 | 6/2011 | Conrad et al. |
| 2012/0046229 A1 * | 2/2012 | Kraynov et al. ......... 514/12.7 |

OTHER PUBLICATIONS

Chan et al., FASEB J. 25:3229-3239, epublished May 20, 2011.*
Pantoni L., Lancet Neurol., 9:689-701, 2010; Kraynov et al., US 2012/0046229 published Feb. 2011.*
Lammie et al., Stroke, 28:2222-2229, 1997.*
McKinley et al, TEM, 9(9): 349-354, 1998.*
St. Louis and Massicotte, Chronic Decrease of Blood Pressure by Rat Relaxin in Spontaneous Hypertensive Rats, Life Sciences, 37:1351-1357, 1985.*
Gons et al., Stroke, 41:2801-2806, 2010.*
Chang et al. Sichuan Da Xue Xue Bao Yi Xue Ban, 42(6):866-9, Nov. 2011 [abstract only].*
Desmond et al., The natural history of CADASIL: a pooled analysis of previously published cases. Stroke 30, 1230-1233, 1999.*
Baumbach et al., Structure of cerebral arterioles in mice deficient in expression of the gene for endothelial nitric oxide synthase. Circ Res. Oct. 15, 2004;95(8):822-9. Epub Sep. 23, 2004.
Beyer et al., Interference with PPARgamma signaling causes cerebral vascular dysfunction, hypertrophy, and remodeling. Hypertension. Apr. 2008;51(4):867-71. doi: 10.1161/HYPERTENSIONAHA.107.103648. Epub Feb. 19, 2008.
Chan et al., Determination of PPARγ activity in adipose tissue and spleen. J Immunoassay Immunochem. 2012;33(3):314-24. Doi: 10.1080/15321819.2011.647189.
Cipolla et al., Inhibition of PPARγ during pregnancy causes inward remodeling of brain parenchymal arterioles. FASEB J Apr. 2010;24(Meeting Abstract Supplement):979.4.
Cipolla et al., SKCa and IKCa Channels, myogenic tone, and vasodilator responses in middle cerebral arteries and parenchymal arterioles: effect of ischemia and reperfusion. Stroke. Apr. 2009;40(4):1451-7. doi: 10.1161/STROKEAHA.108.535435. Epub Feb. 26, 2009.
Cipolla et al., Pregnancy and PPARγ activation cause small vessel remodeling in the maternal brain and diminished cerebrovascular resistance: a role in eclampsia? Reprod Sci. 2009; 16:91A.
Cipolla et al., Perivascular innervation of penetrating brain parenchymal arterioles. J Cardiovasc Pharmacol. Jul. 2004;44(1):1-8.
Desouza et al., Effects of a PPAR-gamma agonist, on growth factor and insulin stimulated endothelial cells. Vascul Pharmacol. Aug.-Sep. 2009;51(2-3):162-8. doi: 10.1016/j.vph.2009.05.001. Epub Jun. 9, 2009.
Gundlach et al., Relaxin family peptides and receptors in mammalian brain. Ann N Y Acad Sci. Apr. 2009;1160:226-35. doi: 10.1111/j.1749-6632.2009.03956.x.
Halabi et al., Interference with PPAR gamma function in smooth muscle causes vascular dysfunction and hypertension. Cell Metab. Mar. 2008;7(3):215-26. doi: 10.1016/j.cmet.2007.12.008.
Ambergy et al., 2010, "Plasma From Preeclamptic Women Increases Blood-Brain Barrier Permeability," Hypertension, p. 1003-1008.
Chan et al., 2010, "Effect of PPARγ inhibition during pregnancy on posterior cerebral artery function and structure," Frontiers in Physiology, 1:130, p. 1-8.
Cipolla et al., 2010, "Cerebral vascular adaptation to pregnancy and its role in the neurological complications of eclampsia," J Appl Physiol 110:329-339.

(Continued)

*Primary Examiner* — Daniel E Kolker
*Assistant Examiner* — Stacey N MacFarlane
(74) *Attorney, Agent, or Firm* — Wolf, Greenfield & Sacks, P.C.

(57) ABSTRACT

The invention relates to methods for modulating PPAR-γ activity using relaxin or agonists thereof. The result is wide range of new therapeutic regimens for treating, inhibiting the development of, or otherwise dealing with, a multitude of illnesses and conditions, including small vessel disorders of the brain and those associated with increased blood-brain barrier permeability, cognitive disorders such as Alzheimer's disease, vascular dementia, epilepsy, stroke, CADASIL and migraine.

12 Claims, 9 Drawing Sheets

(56) References Cited

OTHER PUBLICATIONS

Cipolla et al., 2010, "PPARγ Activation Prevents Hypertensive Remodeling of Cerbral Arteries and Improves Vascular Function in Female Rats," Stroke, 41:1266-1270.

Faraci, F., 2010, "Protecting against vascular disease in brain," Am J. Physiol Heart Circ Physiol 300: H1566-H1582.

Roberts et al, 2009, "PPARγ agonist rosiglitazone reverses increased cerebral venous hydraulic conductivity during hypertension," Am J Physiol Heart Circ Physiol, 297: H1347-H1353.

Schreurs et al., 2012, "The adaptation of the blood-brain barrier to vascular endothelial growth factor and placental growth factor during pregnancy," FASEB J., 26:355-362.

Teerlink et al., 2009, "Relaxin for the treatment of patients with acute heart failure (Pre-RELAX-AHF): a multicenter, randomized, placebo-controlled, parallel-group, dose-finding phase IIb study," Lancet, V. 373, p. 1429-1439.

van Norden et al., 2011, "Causes and consequences of cerebral small vessel disease. The RUN DMC study: a prospective cohort study. Study rationale and protocol.", BMC Neurology 11:29 p. 1-8.

\* cited by examiner

Figure 6
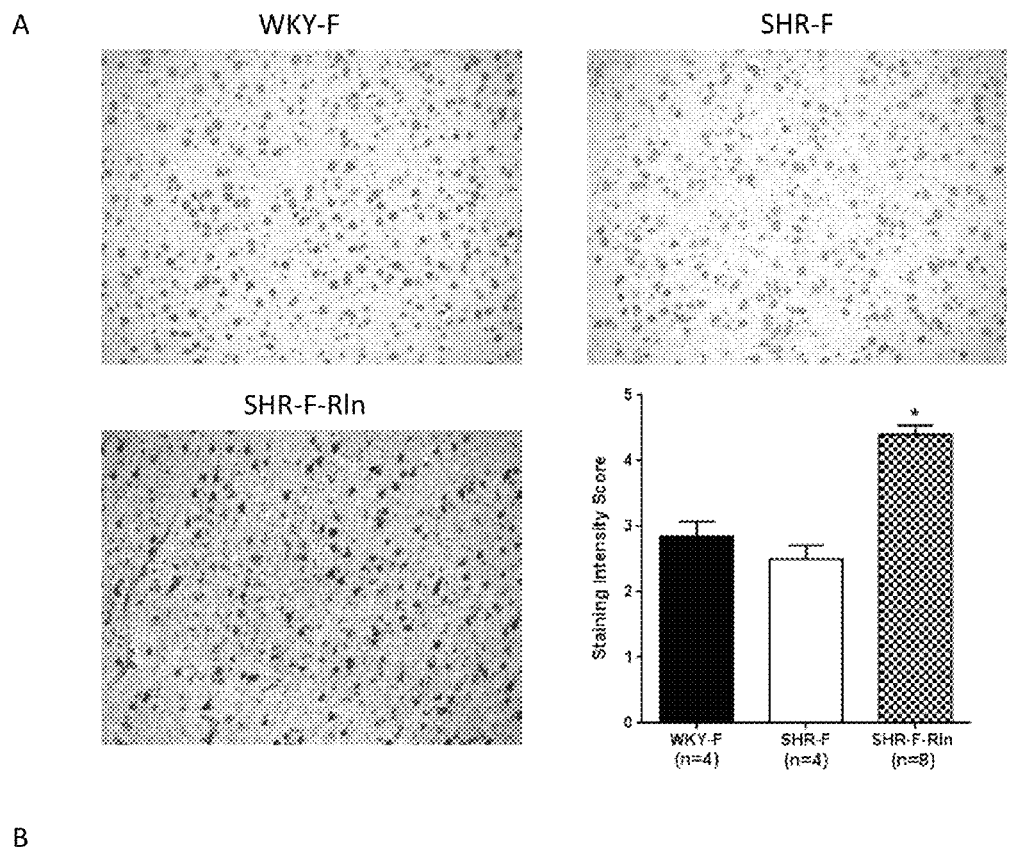
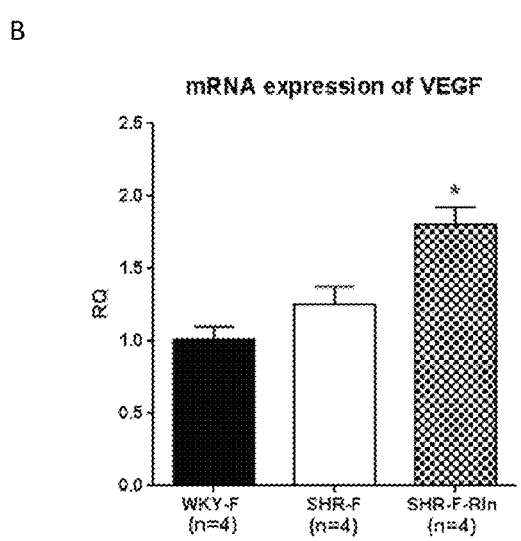

«METHODS OF TREATING DISEASES ASSOCIATED WITH PPARγ»

RELATED APPLICATIONS

This application claims priority under 35 U.S.C. §119(e) to U.S. Provisional Application Ser. No. 61/652,406, entitled "METHODS OF TREATING DISEASES ASSOCIATED WITH PPARΓ" filed on May 29, 2012 which is herein incorporated by reference in its entirety.

FEDERALLY SPONSORED RESEARCH

This invention was made with Government support under RO1 NS045940; RO1 NS043316; PO1 HL095488 awarded by the National Institutes of Health. The Government has certain rights in this invention.

BACKGROUND OF INVENTION

Relaxin is a small peptide hormone primarily produced by the ovaries and placenta during pregnancy (Sherwood (2004) *Endocr Rev* 25, 205-234). Three relaxin genes have been identified in humans, designated as H1, H2, and H3 relaxin. H2 relaxin is the major circulating relaxin that is substantially increased during pregnancy (Sherwood (1994) In The Physiology of Reproduction (Knobil, E., and Neill, J. D., eds) Vol. 1 pp. 861-1009). H2 relaxin binds to relaxin family peptide receptor 1 (RXFP1, previously known as LGR7) with high affinity (Bathgate et al., (2006) *Pharmacol Rev* 58, 7-31). A growing amount of literature suggests that relaxin has extensive cardiovascular effects even outside of pregnancy, such as promoting vasodilation and angiogenesis, and protecting against fibrosis and inflammation in systemic and renal circulations (Bani, (2008) *Vasc Health Risk Manag* 4, 515-524; Conrad et al. (2004) *Am J Physiol Regul Integr Comp Physiol* 287, R250-261). Recently, the therapeutic potential of relaxin has been suggested for treatment of heart failure and preeclampsia (Teerlink et al., (2009) *Lancet* 373, 1429-1439; Unemori et al., (2009) *Ann N Y Acad Sci* 1160, 381-384).

SUMMARY OF INVENTION

The invention is based at least in part on the discovery that relaxin and agonists thereof cause outward remodeling of brain arterioles, increase the number of capillaries in the brain and reduce blood-brain barrier (BBB) permeability. These effects are mediated through a peroxisome proliferator-activated receptor-γ (PPARγ)-based mechanism. In some aspects the invention is a method for treating a small vessel disease of the brain, by chronically administering to a subject having a small vessel disease of the brain relaxin or agonist thereof, wherein the subject is not otherwise in need of treatment with relaxin or agonist thereof in an effective amount to promote outward remodeling of the small vessels of the brain, increase brain capillary density or decrease BBB permeability. In some embodiments the subject has CADASIL (cerebral autosomal dominant arteriopathy with subcortical infarcts and leukoencephalopathy).

In other aspects, the invention is a method for treating a small vessel disease of the brain, by identifying a subject as having small vessel disease of the brain and administering to the subject a relaxin or agonist thereof.

In other aspects the invention is a method for treating a disease of the brain, by identifying a subject as having a disease of the brain and administering to the subject a relaxin or agonist thereof in a neuroprotective effective amount.

A method for treating a subject having a migraine by systemically administering to a subject having a migraine a relaxin or agonist thereof is provided according to other aspects of the invention.

A method for treating a cognitive disorder by systemically administering to a subject having a cognitive disorder a relaxin or agonist thereof is provided in other aspects of the invention. In some embodiments the cognitive disorder is Alzheimer's disease.

The relaxin or agonist thereof is, in some embodiments, recombinant human relaxin.

In some embodiments the subject is further administered a PPAR-γ agonist, such as, for instance, a thiazolidinedione.

The relaxin or agonist thereof may be administered to the subject by any known route of administration. For instance it may be delivered systemically. In some embodiments the relaxin or agonist thereof is administered to the subject, orally, transdermally or subcutaneously.

In other embodiments the relaxin or agonist thereof is administered to the subject in a sustained release formulation.

A method for treating diabetes is provided in other aspects of the invention. The method involves administering to a subject having diabetes a relaxin or agonist thereof. In some embodiments the subject does not have fibrotic disease. In other embodiments the subject is not pregnant. In yet other embodiments the relaxin or agonist thereof is administered chronically. The relaxin or agonist thereof is administered systemically in other embodiments.

The relaxin may be administered to the subject at a predetermined rate so as to maintain a serum concentration of at least about 1 ng/ml, in certain embodiments.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6 is a set of graphs showing the effect of relaxin on expression of VEGF in brain cortex during hypertension. Graphs showing A) representative photomicrographs of VEGF immunohistochemistry and quantification of VEGF staining intensity, and B) qPCR analysis of mRNA expression of VEGF of brain cortex from WKY-F, SHR-F and SHR-F treated with relaxin (SHR-F-Rln). Relaxin significantly increased VEGF immunoreactivity and mRNA expression in brain cortex during hypertension (*p<0.05 vs. SHR-F).

DETAILED DESCRIPTION

Figure 1:
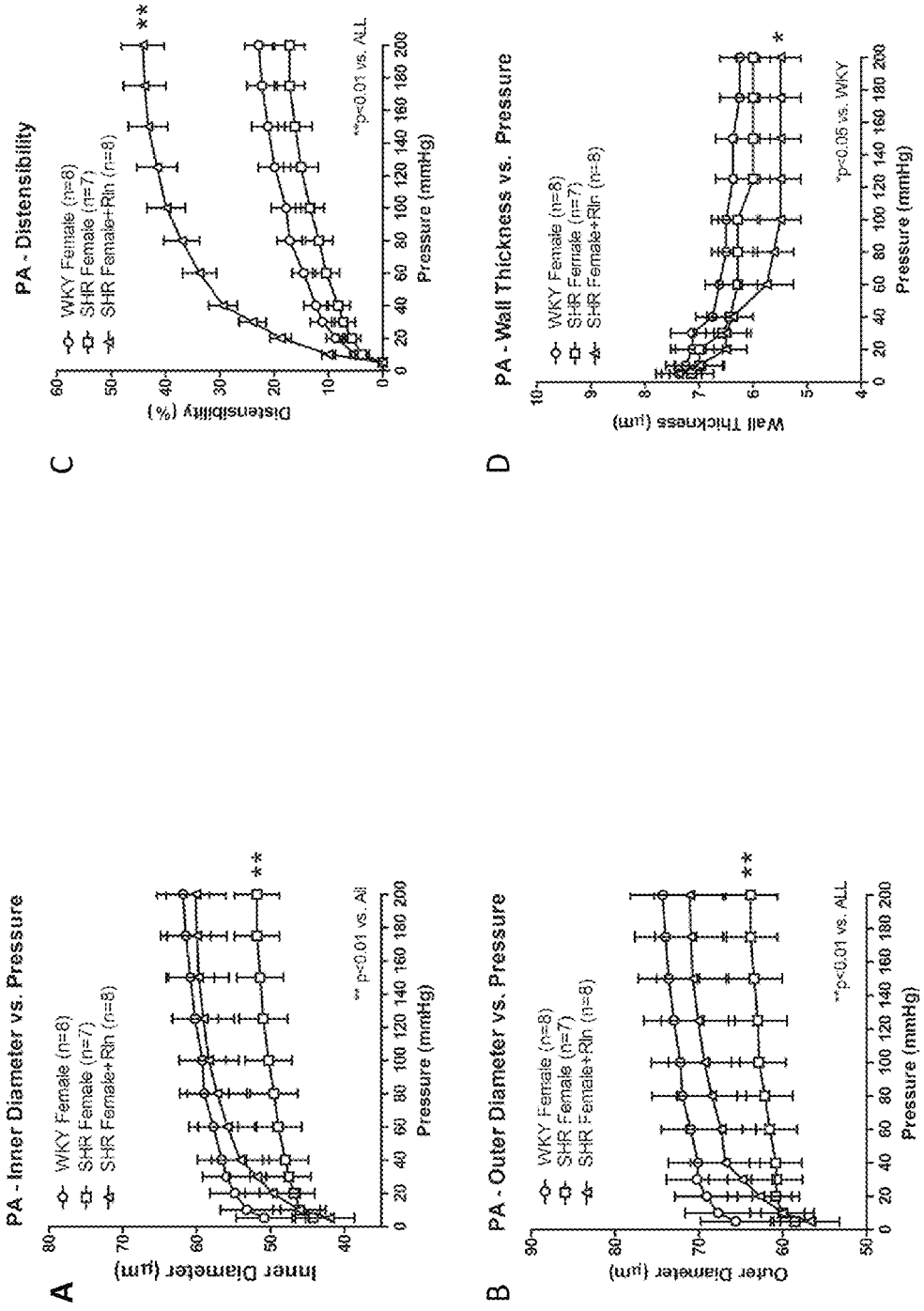
FIG. 1 is a set of graphs showing A) inner diameter (ID) versus pressure, B) outer diameter (OD) versus pressure, C) PA distensibility, and D) PA wall thickness versus pressure for parenchymal arterioles (PA).

It was discovered herein that relaxin promotes selective outward remodeling in parenchymal arterioles (PA) and increases capillary density in the brain. The data shown in the Examples involves a comparison of the structural and functional changes in capillaries, PA and MCA from vehicle- and relaxin-treated NP rats to the level of mid-term pregnancy. Similar to the changes observed naturally during pregnancy, it was demonstrated that relaxin induces an increase in capillary density (increased number of capillaries) in the brain and selective outward remodeling of brain PA but not larger pial arteries. This outward remodeling is characterized by increased inner diameter and decreased wall thickness. The cerebral circulation is unique in that the large arteries contribute significantly to vascular resistance in the brain. Thus, the unchanged size of the large arteries suggests that normal vascular resistance blood flow in the brain may be maintained in response to relaxin therapy.

It was also determined, according to aspects of the invention, that the selective remodeling of PA induced by relaxin was achieved through activation of peroxisome proliferator-activated receptor-γ (PPARγ). The data were generated by treating rats with a PPARγ inhibitor GW9662 in addition to relaxin to determine if the inhibitor would prevent relaxin-induced remodeling. The effect of relaxin and relaxin plus GW9662 on PPARγ target genes to determine if relaxin activates PPARγ was also assessed, as shown in the Examples. PPARγ is a nuclear receptor transcription factor shown to be involved in structural remodeling of the cerebral circulation. PPARγ is highly activated during pregnancy and involved in placental development and changes in maternal metabolism. PPARγ in non-pregnant (NP) rats also causes outward remodeling of PA similar to pregnancy. Additionally, pharmacological inhibition of PPARγ in late-pregnant rats inhibits this outward remodeling in PA.

The impact of hypertension on the function and structure of cerebral parenchymal arterioles (PA), a major target of cerebral small vessel disease (SVD) and the role of relaxin as a treatment for SVD during hypertension was also studied. As shown in the examples, PA were isolated and pressurized from 18-week-old female normotensive Wistor-Kyoto (WKY), spontaneous hypertensive rats (SHR), SHR treated with human relaxin-2 for 14 days (4 µg/hr; n=8/group). Hypertension reduced PA inner diameter (58±3 vs. 49±3 µm in WKY, p<0.05), suggesting inward remodeling that was reversed by relaxin (56±4 µm, p<0.05). Relaxin also increased PA distensibility in SHR (34±2 vs. 10±2% in SHR-F, p<0.05). Relaxin was detected in cerebrospinal fluid (110±30 pg/ml) after systemic administration suggesting it crosses the blood-brain barrier (BBB). Relaxin receptors (RXFP1/2) were not detected in cerebral vasculature. Relaxin treatment, however, resulted in increased vascular endothelial growth factor (VEGF) and matrix metalloproteinase-2 (MMP-2) expression in brain cortex Inhibition of VEGF receptor tyrosine kinase (axitinib, 4 mg/kg/day, 14 days) had no effect on increased distensibility with relaxin, but caused outward hypertrophic remodeling of PA from SHR. These results suggest that relaxin crosses BBB and activates gene expression in brain cortex, which may result in increased distensibility. VEGF appears to be involved in remodeling of PA, but not relaxin-induced increased distensibility.

These discoveries have important implications in the treatment of small vessel disease (SVD) of the brain, conditions that increased BBB permeability and diseases associated with reduced PPARγ activity. Diseases associated with SVD of the brain and increased BBB permeability include lacunar stroke, white matter lesions (leukoaraiosis), migraine, and cognitive disorders such as Alzheimer's disease and vascular dementia. Thus, the invention includes methods of treating subjects having SVD of the brain and diseases associated with reduced PPARγ activity.

A subject shall mean a human or vertebrate mammal including but not limited to a dog, cat, horse, goat and primate, e.g., monkey. Thus, the invention can also be used to treat diseases or conditions in non human subjects. Preferably the subject is a human. In some embodiments the subject is one who is not otherwise in need of treatment with relaxin or an agonist thereof. Therefore the subject, in specifically identified embodiments, may be one who has not been previously diagnosed with a disorder for which relaxin is an identified form of treatment.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

A SVD of the brain, as used herein is a disorder associated with mild to moderate or severe cognitive impairment and in some instances recurrent falling due to gait and balance disturbances. SVD is related to vascular risk factors and cognitive and motor impairment, ultimately leading to dementia. Typically, SVD can be visualized on MRI as white matter lesions (WML) and lacunar infarcts. The presence of brain infarcts and the severity of WML and generalized brain atrophy on MRI are indicative of the disease and are associated with an increased risk of dementia. SVD is also associated with increased blood brain barrier (BBB) permeability. The compounds of the invention are PPARγ agonists, and may contribute to the treatment of SVD by improving endothelial function and decreasing BBB permeability.

The subject may be first identified as a subject having SVD and then treated with relaxin or agonists thereof. The skilled artisan is aware of methods for identifying a subject as having SVD.

In some embodiments the SVD is CADASIL (cerebral autosomal dominant arteriopathy with subcortical infarcts and leukoencephalopathy). CADASIL is a neurovascular disease believed to be caused by one or more mutations of the human Notch3 gene. This condition is characterized by recurrent subcortical ischemic strokes and dementia. It is underlaid by a cerebral non-atherosclerotic, non-amyloid angiopathy affecting mainly the small arteries penetrating the white matter and basal ganglia. A subject having CADASIL can be diagnosed in several different ways, including, by analyzing the skin using electron microscopic examination, by magnetic resonance imaging (MRI) of the brain or by using genetic testing for one or more Notch3 gene mutations.

A disease associated with reduced PPARγ activity as used herein is a disorder in which PPARγ activity plays some role in the development, maintenance or worsening of the disorder. Such diseases can be effectively treated by administering an activator of PPARγ activity including relaxin. Diseases associated with reduced PPARγ activity include but are not limited to diabetes, migraine, and cognitive disorders such as Alzheimer's disease. In some embodiments the disease associated with reduced PPARγ activity is not diabetes. In other embodiments the disease associated with reduced PPARγ activity is a disease of the brain.

Several of these diseases of the brain are associated with increased BBB permeability. For instance, BBB permeability has been associated with epilepsy, Alzheimer's disease, migraine, leukoaraiosis, and hypertension. We have demonstrated that PPARγ activation prevents increased BBB permeability in hypertension. Since relaxin activates PPARγ it is expected to prevent increased BBB permeability in conditions that cause it, such as Alzheimer's disease, migraine, lacunar stroke and leukoaraiosis.

The compounds of the invention are useful for treating diabetes. Diabetes Mellitus is a syndrome of disordered metabolism and refers to the group of diseases that are associated with high blood glucose levels (hyperglycemia) due to defects in either insulin secretion (Type 1) or insulin sensitivity (Type 2). Hyperglycemia tends to be associated with the acute forms of diabetes (such as diabetic ketoacidosis and hyperglycemia hyperosmolar state) and chronic forms and related complications (such as microangiopathy (including retinopathy, neuropathy, nephropathy and cardiomyopathy)) and macrovascular disease (including coronary artery disease, stroke, peripheral vascular disease, myonecrosis). The relaxin compounds described herein treat the diabetes through the PPARg receptor rather than through altering arterial stiffening.

Migraine is a disorder that is characterized by pain in the head, often exacerbated by movement or physical activity, nausea and/or vomiting, diarrhea, photophobia, visual disturbances, including scintillating appearances of light, alternations in consciousness including seizure, syncope, and confused state, vertigo, light-headedness, scalp tenderness, or paresthesia. Relaxin is useful in treating migraine.

The relaxin or agonist thereof of the invention are also useful in treating Alzheimer's disease Alzheimer's disease is a degenerative brain disorder characterized by cognitive and noncognitive neuropsychiatric symptoms, which accounts for approximately 60% of all cases of dementia for patients over 65 years old. Psychiatric symptoms are common in Alzheimer's disease, with psychosis (hallucinations and delusions) present in many patients. It is possible that the psychotic symptoms of Alzheimer's disease involve a shift in the concentration of dopamine or acetylcholine, which may augment a dopaminergic/cholinergic balance, thereby resulting in psychotic behavior. For example, it has been proposed that an increased dopamine release may be responsible for the positive symptoms of schizophrenia. This may result in a positive disruption of the dopaminergic/cholinergic balance. In Alzheimer's disease, the reduction in cholinergic neurons effectively reduces acetylcholine release resulting in a negative disruption of the dopaminergic/cholinergic balance. Relaxin increases capillary density in the brain that could prevent the loss of cholinergic neurons in Alzheimer's disease.

In some embodiments it is important to administer the compounds systemically. It has been shown according to the invention that systemic administration is sufficient to deliver the compounds to the brain, such that they can induce outward remodeling of the vessels of the brain.

The compounds useful according to the invention are relaxin and agonists thereof. Relaxin is an insulin-like peptide having two separate chains (A and B) joined by two interchain and one intrachain disulfide bond. The polypeptide relaxin includes human H1, H2 and H3 preprorelaxin, prorelaxin, and relaxin and recombinant human relaxin (rhRLX). Human relaxin amino acid sequences known in the art. For instance, the sequences are disclosed in GenBank Accession Nos.: Q3WXF3, human H3 prorelaxin; P04808, human H1 prorelaxin; $NP_{604390}$ and $NP_{005050}$, human H2 prorelaxin; AAH05956, human relaxin 1 preproprotein; $NP_{008842}$, human H1 preprorelaxin.

As used herein, the terms "relaxin" and "agonists thereof" are used together or interchangeably to refer to biologically active relaxin polypeptides from recombinant or native (e.g., naturally occurring) sources; relaxin polypeptide variants, such as amino acid sequence variants; synthetic relaxin polypeptides; as well as non-peptide relaxin receptor agonists.

Relaxin agonists include but are not limited to relaxin polypeptides having A and B chains having N- and/or C-terminal truncations. For example, in H2 relaxin, the A chain can be varied from A(1-24) to A(10-24) and B chain from B(1-33) to B(10-22); and in H1 relaxin, the A chain can be varied from A(1-24) to A(10-24) and B chain from B(1-32) to B(10-22). Other relaxin analogs are disclosed in U.S. Pat. Nos. 5,759,807; 5,811,395; 5,945,402; and 6,200,953 as well as US Published Patent Applications 20030158376; 20110130332; and 20120046229.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

The pharmaceutical compositions may also be sterile in some embodiments. In other embodiments the compounds of the invention may be isolated. As used herein, the term "isolated" means that the referenced material is removed from its native environment, e.g., a cell. Thus, an isolated biological material can be free of some or all cellular components, i.e., components of the cells in which the native material occurs naturally (e.g., cytoplasmic or membrane component). In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" in reference to a protein or a nucleic acid, refers to the separation of the desired substance from contaminants to a degree sufficient to allow the practitioner to use the purified substance for the desired purpose. Preferably this means at least one order of magnitude of purification is achieved, more preferably two or three orders of magnitude, most preferably four or five orders of magnitude of purification of the starting material or of the natural material. In specific embodiments, a purified relaxin or agonist thereof is at least 60%, at least 80%, or at least 90% of total protein or nucleic acid, as the case may be, by weight. In a specific embodiment, a purified relaxin or agonist thereof is purified to homogeneity as assayed by, e.g., sodium dodecyl sulfate polyacrylamide gel electrophoresis, or agarose gel electrophoresis.

In some embodiments a purified and or isolated molecule is a synthetic molecule. Synthetic relaxin or agonists thereof are well known in the art.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment. Multiple doses of the molecules of the invention are also contemplated.

The relaxin or agonists thereof may be used alone without other active therapeutics or may be combined with other therapeutic compounds for the treatment of the diseases described herein. For instance the compositions described herein may be combined with PPARγ activators. A PPARγ activator as used herein is any compound that activates the PPARγ receptor. The relaxin or agonist thereof may also be administered in combination with an anti-diabetic agent (including PPARγ activators), an agent for treating small vessel disease of the brain, an anti-migraine agent or an Alzheimer's medicament. Anti-diabetic agents include, for example, thiazolidinediones (e.g. trogliazone, pioglitazone, englitazone, rosiglitazone); biguanides such as phenformin and metformin; protein tyrosine phosphatase 1-B inhibitors; insulin or insulin mimetics; sulfonylureas such as tolbutamide and glipizide; and glucosidase inhibitors such as miglitol, voglibose and acarbose. Anti migraine agents include triptans which are selective serotonin 5-HT1B/1D agonists and analgesics, e.g. NSAIDs.

When used in combination with the therapies of the invention the dosages of known therapies may be reduced in some instances, to avoid side effects. In some instances, when the molecules of the invention are administered with another therapeutic, for instance, anti-diabetic agents a sub-therapeutic dosage of either the molecules or the anti-diabetic agents, or a sub-therapeutic dosage of both, is used in the treatment of a subject having, or at risk of developing diabetes. When the two classes of drugs are used together, the anti-diabetic agents may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of an anti-diabetic agent is one which would not produce the desired therapeutic result in the subject in the absence of the administration of the molecules of the invention. Therapeutic doses of anti-diabetic agents are well known in the field of medicine for the treatment of diabetes. These dosages have been extensively described in references such as Remington's Pharmaceutical Sciences; as well as many other medical references relied upon by the medical profession as guidance for the treatment of diabetes.

The relaxin or agonist thereof can be administered in combination with other therapeutic agents and such administration may be simultaneous or sequential. When the other therapeutic agents are administered simultaneously they can be administered in the same or separate formulations, but are administered at the same time. The administration of the other therapeutic agent and the relaxin or agonist thereof can also be temporally separated, meaning that the therapeutic agents are administered at a different time, either before or after, the administration of the relaxin or agonist thereof. The separation in time between the administration of these compounds may be a matter of minutes or it may be longer. For instance the relaxin or agonist thereof may be administered in combination with a diabetes therapy such as a thiazolidinedione.

In some aspects, the invention provides methods and kits that include relaxin or agonist thereof and anti-diabetic agents.

The relaxin or agonist thereof and anti-diabetic agents described herein can be used alone or in conjugates with other molecules such as detection agents in the detection and treatment methods of the invention, as described in more detail herein.

The active agents of the invention are administered to the subject in an effective amount for treating disorders such diabetes, migraine, Alzheimer's disease and small vessel disease of the brain. An "effective amount", for instance, is an amount necessary or sufficient to realize a desired biologic effect. An "effective amount for treating Alzheimer's disease", for instance, could be that amount necessary to (i) reduce memory loss by a patient and/or (ii) inhibit the further development of memory loss, i.e., arresting or slowing its development. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. In some embodiments the effective amount is an amount that is effective for promoting outward remodeling of the small vessels of the brain.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be non-toxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition of the invention can be used directly or can be mixed with suitable adjuvants and/or carriers. Suitable adjuvants include aluminum salt adjuvants, such as aluminum phosphate or aluminum hydroxide, calcium phosphate nanoparticles (BioSante Pharmaceuticals, Inc.), ZADAXIN™, nucleotides ppGpp and pppGpp, killed *Bordetella pertussis* or its components, *Corenybacterium* derived P40 component, cholera toxin and mycobacteria whole or parts, and ISCOMs (DeVries et al., 1988; Morein et al., 1999 & Lovgren: al., 1991). Also useful as adjuvants are Pam3Cys, LPS, ds and ss RNA. The skilled artisan is familiar with carriers appropriate for pharmaceutical use or suitable for use in humans.

The composition of the invention can be administered in various ways and to different classes of recipients. In some instances the administration is chronic. Chronic administration refers to long term administration of a drug to treat a disease. The chronic administration may be on an as needed basis or it may be at regularly scheduled intervals. For instance, the relaxin or agonists thereof may be administered daily, weekly, monthly quarterly etc.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. Pharmaceutically-acceptable carriers for relaxin and agonists thereof are well-known to those of ordinary skill in the art. As used herein, a pharmaceutically-acceptable carrier means a non-toxic material that does not interfere with the effectiveness of the biological activity of the active ingredients, e.g., the ability of the relaxin to promote increased capillary density, outward remodeling of brain arterioles and/or PPARγ activation in these vessels.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases or recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations of the peptides may be prepared for storage by mixing a peptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of diabetes, migraine, small vessel disease of the brain or Alzheimer's disease.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The kits, in one set of embodiments, may comprise a carrier being compartmentalized to receive in close confinement one or more containers such as vials, tubes, and the like, each of the containers comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said pharmaceutical agent is a relaxin or a derivative, fragment, homolog, analog thereof and a pharmaceutically acceptable carrier, and said instructions indicate a dosing regimen for preventing, treating or managing a subject with diabetes, migraine, small vessel disease of the brain or Alzheimer's disease.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Materials and Methods

Animals and Treatment Groups: All procedures were approved by the Institutional Animal Care and Use Committee and conducted in accordance with the National Institutes of Health Guide for the Care and Use of Laboratory Animals. Female virgin NP Sprague Dawley rats (250-300 g, 14-16 weeks, Charles River, Canada) were used for all experiments and housed in the University of Vermont Animal Care Facility. Animals were randomly selected and grouped as untreated (N=4), treated with recombinant human relaxin-2 (relaxin, 4 µg/hr; N=14), relaxin plus a specific PPARγ inhibitor GW9662 (10 mg/kg daily in food; N=8), or vehicle (20 mM sodium acetate; N=14) for 10 days through osmotic minipumps (Alzet 2ML2, Durect Corp., Cupertino, Calif., USA). GW9662 treatment was started 1 day before and for the duration of relaxin treatment to ensure PPARγ was inhibited. Animals were anesthetized with 3% isoflurane and minipumps implanted subcutaneously in the back of the neck. All animals received post-surgical analgesic (buprenorphine, 50 µg/kg, s.c.). Relaxin infusion was continuous for 10 days until animals were euthanized for vessel experiments and tissue collection. The minipumps used were capable of delivering relaxin for 14 days and thus tissue collection was within this duration.

Female SHR and female normotensive Wistar-Kyoto rats (WKY) (190-220 g, 14-16 weeks, Charles River, Canada) were also used and housed in the University of Vermont Animal Care Facility Animals were randomly selected and grouped as untreated WKY (WKY-F, n=8), untreated SHR (SHR-F, n=8), SHR treated with recombinant human relaxin-2 (relaxin, 4 µg/hr) for 14 days via osmotic minipump (Alzet 2ML2, Durect Corp., Cupertino, Calif., USA) (SHR-F-Rln, n=8), SHR co-treated with relaxin plus a non-selective VEGF receptor (VEGF-R) tyrosine kinase inhibitor axitinib (2 mg/kg, twice a day in food, 14 days) (SHR-F-Rln-Axi, n=8). A separate group of SHR-F was used to determine if relaxin crosses the BBB by treating with relaxin (4 µg/hr) for 14 days and measuring relaxin concentration in cerebrospinal fluid (CSF) and serum (SHR-F-Rln-CSF, n=4). For the osmotic pump implant, animals were anesthetized with 3% isoflurane and minipumps implanted subcutaneously in the back of the neck. All animals received post-surgical analgesia (buprenorphine, 50 µg/kg, s.c.). Relaxin infusion was continuous for 14 days until animals were euthanized for isolated vessel experiments and tissue collection.

Determination of Relaxin Levels in Serum: Vehicle-, relaxin-, and relaxin+GW9662-treated animals were anesthetized with isoflurane (3% in oxygen), decapitated, and trunk blood was collected for measurement of circulating relaxin. Serum was then collected and stored at −80° C. for determination of relaxin levels by ELISA following manufacturer's instructions (Human Relaxin-2 Quantikine ELISA Kit, R&D Systems, Minneapolis, Minn., USA). Serum samples were diluted by 1:500 in the assay.

Vessel Preparation and Pressurized Arteriograph System: After collecting trunk blood, the brain was quickly removed and placed in cold physiological salt solution (PSS). In the first set of experiments, PA between the M1 and M2 region of the MCA territory and the MCA from the same animals were carefully isolated from vehicle- or relaxin-treated animals and mounted on glass cannulas in a dual-chambered arteriograph such that one PA and one MCA from each animal were studied simultaneously. PA were identified as branches off the MCA that penetrated into the brain tissue, as previously described (25). In the second set of experiments, PA from the same brain region as above were dissected from relaxin+GW9662-treated animal and compared to PA from vehicle- and relaxin-treated animals. MCA were not studied in this second set of animals because there was no effect of relaxin on that segment of the vasculature. The proximal cannulas were connected to an in-line pressure transducer and a servo-null pressure control system (Living Systems Instrumentation, Burlington, Vt., USA) that allowed intravascular pressure to be maintained at a set pressure or changed at a variable rate. The distal cannulas were closed during the experiment to avoid flow-mediated responses. Temperature and pH were continuously measured and maintained at 37.0±0.5° C. and 7.40±0.05, respectively. Measurements of inner diameter (ID) and wall thickness (WT) were made via video microscopy (Living Systems Instrumentation).

Vascular Reactivity and Structural Characteristics in PA and MCA: For the first set of experiments, PA and MCA were equilibrated for 1 hour at 25 mmHg, after which myogenic activity was determined by stepwise increases in pressure from 40 to 100 mmHg for PA or 50 to 175 mmHg for MCA. ID and WT were measured at each pressure once stable. Changes in ID and WT were measured in PA only in response to small- (SKCa) and intermediate- (IKCa) conductance calcium-activated potassium channels blockers, apamin ($3 \times 10^{-7}$ M) and TRAM-34 ($10^{-6}$ M), respectively. PA are unique in that the contribution of endothelium-derived hyperpolarizing factors (EDHF) to tone is greater than most vessels Cipolla et al. (2009) $Stroke$ 40, 1451-1457. Thus, inhibition of SKCa/IKCa channels, a critical component in the EDHF pathway, causes constriction in PA Cipolla et al. (2009) $Stroke$ 40, 1451-1457. We therefore assessed the effect of relaxin on constriction of PA in response to SKCa/IKCa channel inhibition in order to assess this unique pathway. To obtain structural measurements, ID and WT were recorded at pressures between 5 to 200 mmHg for PA or 5 to 175 mmHg for MCA after papaverine ($10^{-4}$ M) and diltiazem ($10^{-5}$ M) were added to the bath. For the second set of experiments in which animals were treated with relaxin+GW9662, passive structural measurements were made as described above.

Determination of RXFP1 and PPARγ Target Gene Expression: MCA and PA from 4 untreated rats were collected to determine expression level of RXFP1, the primary relaxin receptor, using real-time qPCR methods. We also collected adipose tissue, pial arteries, and PA from vehicle, relaxin and relaxin+GW9662 groups (n=6 for each group) for determination of PPARγ target gene expression. All collected samples were stored in RNase inhibitor (1 unit/µl, RiboLock, Fermentas, Glen Burnie, Md., USA) at −80° C. for comparing expression of fatty acid translocase (FAT)/CD36 and liver X receptors-α (LXRα) for adipose tissue, and plasminogen activator inhibitor-1 (PAI-1) for vasculature. Standard techniques for real-time qPCR were performed by the Vermont Cancer Center DNA analysis facility at the University of Vermont, as described previously Cipolla et al. (2009) $Stroke$ 40, 1451-1457. Briefly, RNA was extracted from tissues and concentration and integrity was determined by a NanoDrop ND-1000 Spectrophotometer (Wilmington, Del.) and an Agilent 2100 Bioanalyzer (Santa Clara, Calif., USA), respectively. Samples with low RNA quality were excluded. cDNA was then made by a SuperScript III Kit (Invitrogen, Carlsbad, Calif., USA). Real-time qPCR was set up as follows: 10 μL Universal PCR Master Mix (Applied Biosystems, Foster City, Calif., USA), 1 μL Assay on Demand (Applied Biosystems), 8 μL water, and 1 μL cDNA. β2-microglobulin (B2M, housekeeping control) and target genes were assessed using Assays on Demand from Applied Biosystems. All primers were validated by the manufacturer for efficiency and did not detect homologs. Primers were designed across an exon-exon junction to avoid detecting genomic DNA. Thus, no DNase treatment of samples was necessary. All samples were run in duplicates using a 7900HT Sequence Detection System (Applied Biosystems). The PCR was cycled for 2 minutes at 50° C., 10 minutes at 95° C., 40 cycles at 95° C. for 15 seconds and then 60° C. for 1 minute.

Drugs and Solutions: All isolated vessel experiments were performed in physiological salt solutions (PSS) containing the following (in mM): 119.0 NaCl, 24.0 NaHCO3, 4.7 KCl, 1.17 MgSO4, 0.026 EDTA, 5.0 CaCl2, 1.18 KH2PO4, and 5.5 glucose and aerated with 5% CO2, 10% O2 and balanced N2 to maintain pH at 7.40±0.05. Relaxin was a generous gift from Corthera Inc (San Carlos, Calif., USA) and Novartis Pharmaceuticals (Basel, Switzerland). GW9662 was from Cayman Chemical (Ann Arbor, Mich., USA). Papaverine and diltiazem were purchased from Sigma (St. Louis, Mo., USA) and were made as stock solutions and stored at 4° C. each week. Apamin and TRAM-34 were purchased from Tocris (Ellisville, Mo., USA) mixed with vehicle, aliquoted and stored at −20° C. until use.

Data Calculations and Statistical Analysis: Percent tone was calculated as percent decrease in ID from the passive diameter at each intravascular pressure: [1−(IDactive/IDpassive)]×100%. Outer diameter (OD) was calculated from measured ID and WT: ID+2WT. Cross-sectional area (CSA) of the wall was calculated as: [(OD/2)2−(ID/2)2]×π. Data from qPCR study were analyzed using the $-2^{\Delta\Delta CT}$ method, as described previously Livak et al. (2001) Methods 25, 402-408. Data were removed when the CT values of technical replicates differed by more than 0.5.

Determination of Conscious Blood Pressure

Systemic blood pressures were determined in all groups of animals using a non-invasive tail-cuff method (Chan, S. L., and Cipolla, M. J. (2011) Relaxin causes selective outward remodeling of brain parenchymal arterioles via activation of peroxisome proliferator-activated receptor-gamma. FASEB J 25, 3229-3239). For untreated WKY-F and SHR-F groups, blood pressures were measured on the day the animals were euthanized. For relaxin treated groups, blood pressures were measured on day 0 (baseline, before pump implant), 2, 7 and 14. All animals were trained for 3 days before actual blood pressure measurements were taken.

Determination of Relaxin Levels in Serum and CSF

Animals were anesthetized with isoflurane (3% in oxygen), decapitated, and trunk blood was collected for measurement of circulating relaxin. Serum was then collected and stored at −80° C. for determination of relaxin levels by enzyme-linked immunosorbent assay (ELISA) following manufacturer's instructions (Human Relaxin-2 Quantikine ELISA Kit, R&D Systems, Minneapolis, Minn., USA). Serum samples were diluted by 1:500 in the assay.

To determine the presence of relaxin in CSF, animals were anesthetized and CSF collected through a needle inserted into the cisterna magna (Liu, L., and Duff, K. (2008) A technique for serial collection of cerebrospinal fluid from the cisterna magna in mouse. Journal of visualized experiments: JoVE). Blood from the same animals was also collected through a catheter inserted to the femoral artery to compare to the concentration of CSF. Relaxin levels were determined in serum and CSF by ELISA as described above, except CSF was not diluted.

Vessel Preparation and Pressurized Arteriograph System

After collecting trunk blood, the brain was quickly removed and placed in cold physiological salt solution (PSS). PA between the M1 and M2 region of the MCA territory and the MCA from the same animals were carefully isolated from WKY-F, SHR-F, and SHR-F-Rln groups and mounted on glass cannulas. PA were identified as branches off the MCA that penetrated into the brain tissue, as previously described (han, S. L., and Cipolla, M. J. (2011) Relaxin causes selective outward remodeling of brain parenchymal arterioles via activation of peroxisome proliferator-activated receptor-gamma. FASEB J 25, 3229-3239). Only PA were studied from the SHR-F-Rln-Axi group because relaxin had no effect on MCA. The proximal cannula was connected to an in-line pressure transducer and a servo-null pressure control system (Living Systems Instrumentation, Burlington, Vt., USA) that allowed intravascular pressure to be maintained at a set pressure or changed at a variable rate. The distal cannula was closed during the experiment to avoid flow-mediated responses. Temperature and pH were continuously measured and maintained at 37.0±0.5° C. and 7.40±0.05, respectively. Measurements of inner diameter (ID) and wall thickness (WT) were made via video microscopy (Living Systems Instrumentation, Burlington, Vt.).

Vascular Reactivity and Structural Characteristics in PA and MCA

PA and MCA were equilibrated for 1 hour, after which myogenic activity was determined by stepwise increases in pressure from 40 to 100 mmHg for PA or 50 to 175 mmHg for MCA. ID and WT were measured at each pressure once stable. Endothelium-dependent dilation was studied by adding NS309 ($10^{-8}$-$10^{-5}$ M), an activator of small- and intermediate-conductance calcium-activated potassium channels ($SK_{Ca}$, $IK_{Ca}$). NS309 was washed out of the bath and a single concentration of the nitric oxide synthase (NOS) inhibitor L-nitro-n-arginine (L-NNA, $10^{-4}$ M) added to the bath. Constriction to NOS inhibition was used as an additional indicator of endothelial function. In the presence of L-NNA, sodium nitroprusside (SNP, $10^{-8}$-$10^{-5}$ M) was added to the bath to assess endothelium-independent vasodilation. To obtain structural measurements, ID and WT were recorded at pressures between 5 to 200 mmHg for PA or 5 to 175 mmHg for MCA in zero-calcium PSS containing ethylene glycol tetraacetic acid (EGTA) and outer diameter (OD) and distensibility calculated.

Quantitative Polymerase Chain Reaction (qPCR) Analysis of Target Gene Expressions After dissecting PA and MCA for isolated vessel experiments, the remaining MCA, PA, and brain cortex from the MCA territory of 4-6 rats were collected and stored at −80° C. in RNase inhibitor (1 unit/μl, RiboLock, Fermentas, Glen Burnie, Md., USA) to determine mRNA expression levels of target genes using real-time qPCR methods. Target genes were assessed using Assays on Demand from Applied Biosystems. All primers were validated by the manufacturer for efficiency and did not detect homologs. All primers were designed across an exon-exon junction to avoid detecting genomic DNA, so no DNase treatment was required. Housekeeping gene β-actin was used in all qPCR experiments as a control. Standard techniques for real-time qPCR were performed by the Vermont Cancer Center DNA analysis facility at the University of Vermont, as described previously (Cipolla, M. J., Smith, J., Kohlmeyer, M. M., and Godfrey, J. A.

(2009) SKCa and IKCa Channels, myogenic tone, and vasodilator responses in middle cerebral arteries and parenchymal arterioles: effect of ischemia and reperfusion. Stroke 40, 1451-1457).

To compare expression levels of relaxin receptors in MCA and PA, RXFP1 and RXFP2 mRNA expression was determined. Due to no expression after 40 cycles of PCR, RNA of selected samples was amplified and expression levels determined again. RNA samples were amplified by Ovation Pico WTA System V2 (NuGEN Technologies, San Carlos, Calif., USA) and the product cDNA was purified by an Agencourt RNAClean XP magnetic bead protocol (Beckman Coulter, Brea, Calif., USA).

To investigate the mechanisms by which relaxin causes selectively remodeling of PA, mRNA expression of VEGF, MMP-2, and MMP-9 were compared between MCA, PA, brain cortex. To determine if relaxin activates peroxisome proliferator-activated receptor-gamma (PPARγ), expression levels of PPARγ target genes fatty acid binding protein-4 (FABP4) and plasminogen activator inhibitor-1 (PAI-1) were determined in mesenteric adipose tissue. Expression levels of PPARγ and its target genes PAI-1 and liver X receptors-α (LXR-α) were also determined in brain cortex (Chan, S. L., and Cipolla, M. J. (2012) Determination of PPARgamma activity in adipose tissue and spleen. J Immunoassay Immunochem 33, 314-324).

Immunohistochemistry of VEGF

Brain cortex from the MCA region from WKY-F, SHR-F and SHR-F-Rln groups was collected and fixed in 4% formaldehyde for 48 hours at 4° C. and embedded in paraffin. Brain cortex was cut into 5 μm sections. After deparaffinization with ethanol, brain cortex sections were washed 3 times with 0.1 M phosphate buffered saline (PBS) and placed in blocking buffer for 5 min (Dual Endogenous Enzyme Block, Dako, Carpinteria, Calif., USA). The sections were incubated with primary antibody against VEGF (1:50, Santa Cruz, Dallas, Tex., USA) diluted in PBS with 1% bovine serum albumin for 30 mM, followed by incubation with secondary antibody using Dako LSAB2 System-Horseradish Peroxidase (Dako) for 20 mM Samples were then treated with 3,3-diaminobenzidine for 4 mM, followed by hematoxylin for 30 sec. After dehydration with ethanol, samples were covered with glass cover slip with xylene-based mounting media. Imaging was performed using Olympus BX50 upright microscope with 20× objective and QImaging Retiga 2000R camera with QCapture Pro 6.0. Staining intensity was assessed using a semi-quantitative scoring system from 0 (lowest staining intensity) to 5 (highest staining intensity) in a blinded fashion. Results were confirmed by grayscale histogram analysis of intensity (0: black-255: white) using Photoshop CS4.

Drugs and Solutions

All isolated vessel experiments were performed in PSS containing the following (mM): 119.0 NaCl, 24.0 NaHCO$_3$, 4.7 KCl, 1.17 MgSO$_4$, 0.026 ethylenediaminetetraacetic acid, 5.0 CaCl$_2$, 1.18 KH$_2$PO$_4$, and 5.5 glucose and aerated with 5% CO$_2$, 10% O$_2$ and balanced N$_2$ to maintain pH at 7.40±0.05. Zero calcium PSS was made by eliminating CaCl$_2$ and a calcium chelator EGTA (10 mM) was added. Relaxin was a generous gift from Corthera Inc (San Carlos, Calif., USA) and Novartis Pharmaceuticals (Basel, Switzerland). L-NNA and SNP were purchased from Sigma (St. Louis, Mo., USA) and were made as stock solutions and stored at 4° C. each week. NS309 was also purchased from Sigma and mixed with dimethyl sulfoxide, aliquoted and stored at −20° C. until use.

Data Calculations and Statistical Analysis

Percent tone was calculated as percent decrease in ID from the passive diameter at each intravascular pressure: $[1-(ID_{active}/ID_{passive})]\times 100$. Percent reactivity for vasodilators was calculated as $((ID_{dose}-ID_{start})/(ID_{passive}-ID_{start}))\times 100$. Percent constriction for vasoconstrictor was calculated as $(1-(ID_{dose}/ID_{start}))\times 100$. OD was calculated from measured ID and WT: ID+2WT. Distensibility at a given pressure was calculated as $(ID_{passive}-ID_{original})/(ID_{original})\times 100$, where $ID_{original}$ is defined as passive inner diameter determined at lowest pressure (5 mmHg). Data from qPCR study were analyzed using the $-2^{\Delta\Delta CT}$ method, as described previously (Livak, K. J., and Schmittgen, T. D. (2001) Analysis of relative gene expression data using real-time quantitative PCR and the 2(−Delta Delta C(T)) Method. Methods 25, 402-408). Data were removed when the Ct values of technical replicates differed by more than 0.5.

All data are presented as mean±SEM. Differences between groups were determined with a Student's t-test for two groups or one-way analysis of variance and a post hoc Newman-Keuls test for multiple comparisons for three or more groups, using Graph Pad Prism 5 (Graph Pad Software Inc., La Jolla, Calif., USA). Differences were considered significant when $p<0.05$.

The data presented in Examples 1-5 is published in Chan and Cippolla FASEB J. 25, 3229-3239 (2011).

Example 1

RXFP1 Gene Expressions and Relaxin Levels in Serum

Real time qPCR revealed that RXFP1 expression was low in middle cerebral arteries (MCA) (threshold cycle: 37.4 vs. 22.2 in the housekeeping gene B2M) and undetectable in parenchymal arteries (PA) (threshold cycle: >40 vs. 25.5 in B2M). Thus, RXFP1 was expressed in MCA, albeit at lower levels than the housekeeping gene, whereas RXFP1 was not highly expressed, if at all, in PA. Because relaxin's effect is specific for PA and capillaries in the brain, vessels with no measureable relaxin receptor, it is likely that the selective effect of this treatment is through a paracrine effect from the brain tissue (neurons, glial cells) acting on the vasculature within the brain parenchyma.

Serum concentrations of relaxin in vehicle-, relaxin, and relaxin+Gw9662-treated animals were measured to confirm the extent of delivery of relaxin. Relaxin treatment increased serum relaxin to the levels between mid and late pregnancy (54±8 ng/ml in relaxin vs. 78±28 ng/ml in relaxin+GW9662 vs. 0.01±0.008 ng/ml in control).

Example 2

Effect of Relaxin on Vascular Reactivity in PA and MCA

We assessed whether relaxin had any effects in cerebral arteries and arterioles. Active diameters in PA and MCA from vehicle- and relaxin-treated rats were assessed. One experiment in the vehicle group and one PA experiment in relaxin group were excluded because of technical issues. PA from both groups of animals displayed myogenic reactivity as ID did not significantly change with pressure. Relaxin treatment caused an increase in diameter of PA at all pressures studied. In contrast, MCA had less myogenic activity than PA and relaxin treatment had no effect on active diameters of MCA at any pressure. In both groups, PA developed greater tone compared with MCA. However, relaxin did not significantly affect tone in either PA or MCA.

The effect of relaxin on endothelial function in cerebral arterioles was also examined. We tested endothelial function through inhibition of $SK_{Ca}$ and $IK_{Ca}$ because these channels are involved in inhibiting tone in PA but not MCA Cipolla et al. (2009) *Stroke* 40, 1451-1457. The effect of apamin and TRAM-34 on ID of PA in both groups of animals was tested. We excluded one PA experiment from the relaxin group because the PA dilated in response to apamin, likely due to depolarization of calcitonin gene-related peptide-containing perivascular nerve fibers that are few on these vessels Cipolla et al., (2004) *J Cardiovasc Pharmacol* 44, 1-8. Apamin induced minimal vasoconstriction in PA while TRAM-34 caused greater vasoconstriction, suggesting a greater influence of $IK_{Ca}$ versus $SK_{Ca}$ channels in inhibiting tone. However, there was no difference between vehicle- and relaxin-treated rats in response to $SK_{Ca}/IK_{Ca}$ inhibition.

Example 3

Effect of Relaxin on the Structure of PA and MCA

In order to study the effect of relaxin on the structure of PA and MCA, we measured ID and WT at various pressures under passive conditions and calculated OD and CSA. In PA, relaxin treatment significantly increased ID at all pressures studied, demonstrating that relaxin caused outward remodeling in PA. Relaxin-induced remodeling of PA was hypertrophic in nature as these vessels also had increased WT and CSA. In addition, relaxin increased OD of PA, confirming that vessels from relaxin-treated rats underwent hypertrophic outward remodeling. The effect of relaxin on structural remodeling appeared to be selective to PA because relaxin had no effect on the structure of MCA.

Example 4

Effect of GW9662 on Relaxin-induced Remodeling in PA

We investigated whether PPARγ has a role in relaxin-induced outward remodeling. We compared the structural properties of PA from vehicle- and relaxin-treated animals to those in which PPARγ was inhibited with GW9662 during relaxin infusions. We compared structural remodeling at a low pressure (5 mmHg) to avoid differences in structure that may be induced by changes in distensibility at higher pressures. We found that treatment with GW9662 prevented the structural changes induced by relaxin. For examples, PA from relaxin+GW9662-treated animals had similar ID, OD, and CSA as vehicle and significantly decreased compared to relaxin treatment alone. WT of PA from relaxin+GW9662 animals was also similar to that of vehicle-treated animals, although this was not statistically significant compared with the relaxin-treated group. Thus, PPARγ inhibition prevented structural remodeling of PA in relaxin-treated animals.

Example 5

PPARγ Target Gene Expression

To confirm activation of PPARγ by relaxin, we determined gene expression of PPARγ target genes in adipose tissue, pial arteries, and PA. In adipose tissue where PPARγ is highly expressed, relaxin decreased gene expression of CD36, which was normalized by GW9662 treatment. A similar trend was observed with LXR-α in adipose tissue, although the changes were not statistically significant. In vascular segments, relaxin did not significantly change PAI-1 in pial arteries or PA. In PA, the low sample numbers were due to both bad RNA quality and high CT variability between replicates and therefore these samples were removed.

Example 6

Figure 2:
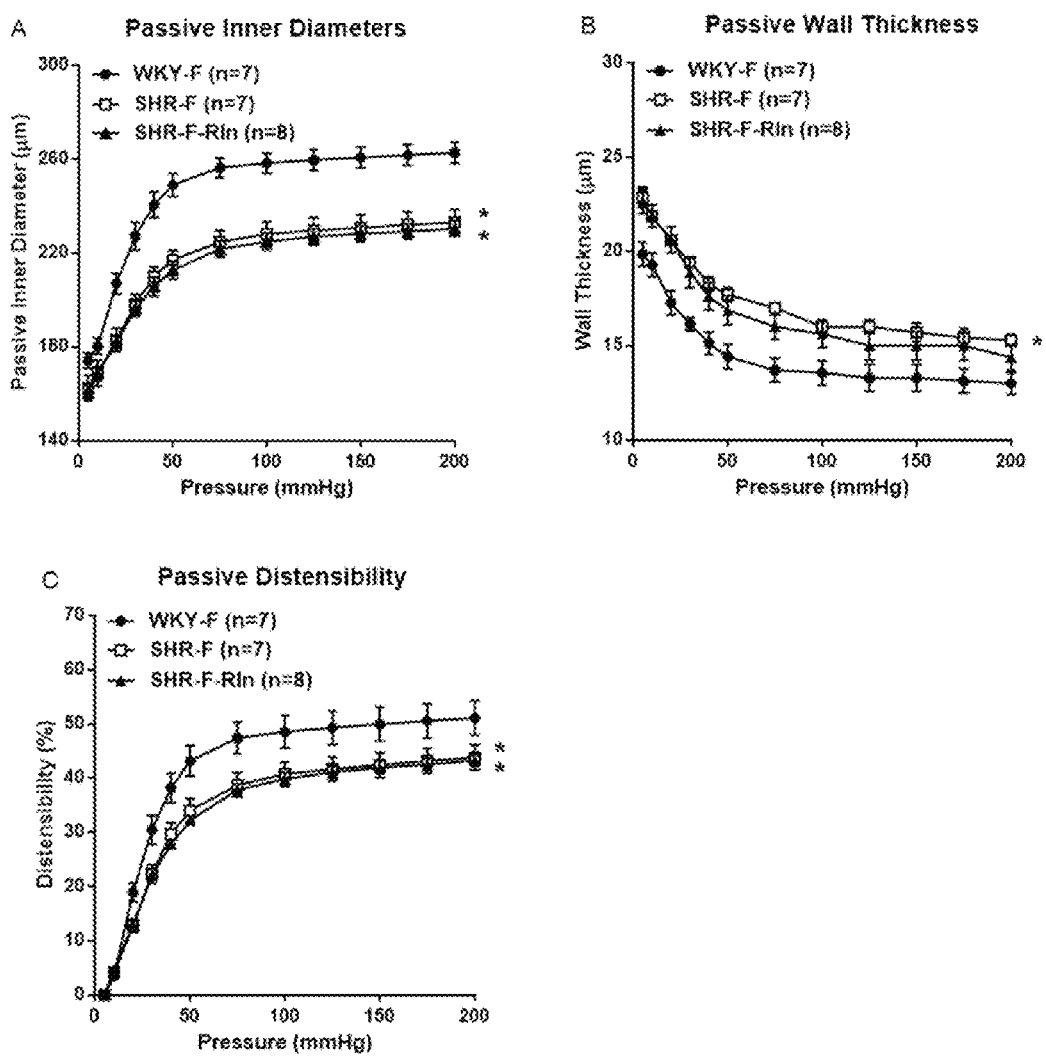
FIG. 2 is a set of graphs showing A) inner diameter (ID) versus pressure, B) PA distensibility, and C) PA wall thickness versus pressure for middle cerebral arteries (MCA).

Effect of Relaxin on PA and MCA Diameter, Distensibility and Wall Thickness in Hypertensive Animals Relaxin had a significant effect on the PA of spontaneously hypertensive rats (SHR) but not the upstream MCA. Interestingly the effects of relaxin were achieved using levels that did not cause a lowering of blood pressure. The data, presented in FIGS. 1 (PA) and 2 (MCA) involve passive measurements, ie., the vessels were given a drug to inactivate the smooth muscle in the arteriole wall so that we can compare the structure of the vessels. The data in FIG. 1 demonstrates that the PA are smaller in the SHR and relaxin treatment increases the size, making them more like the normotensive counterpart (WKY) but only at the higher pressures. Relaxin also showed a big effect on distensibility, a means of measuring stiffness, ie. the vessels were not as stiff and so dilated to the pressure to a greater extent. The data in FIG. 2 shows similar measurements as in FIG. 1 on MCA. In these vessels relaxin had no effect. Therefore, relaxin can selectively affect the parenchymal arterioles.

Example 7

Effect of Relaxin on Brain Capillary Density of Hypertensive Rats

Figure 3:
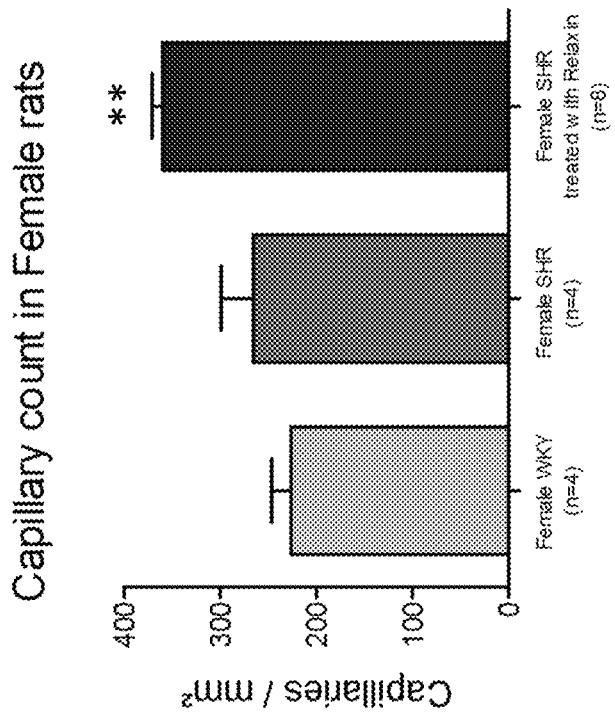
FIG. 3 is a graph of brain capillary density measured from normotensive WKY rats, hypertensive SHR rats, and hypertensive SHR rats treated with relaxin.

In addition to selecting increasing PA size and distensibility, relaxin treatment of SHR rats caused a significant increase in capillary number, as assessed by immunohistochemistry of brain tissue for von Willebrand factor and counting capillaries using a morphometric approach. FIG. 3 shows that relaxin treatment of SHR female rats significantly increased the number of capillaries in the brain vs. WHY and SHR without treatment.

Example 8

Impact of Chronic Hypertension on Function and Structure of PA and MCA

Figure 4:
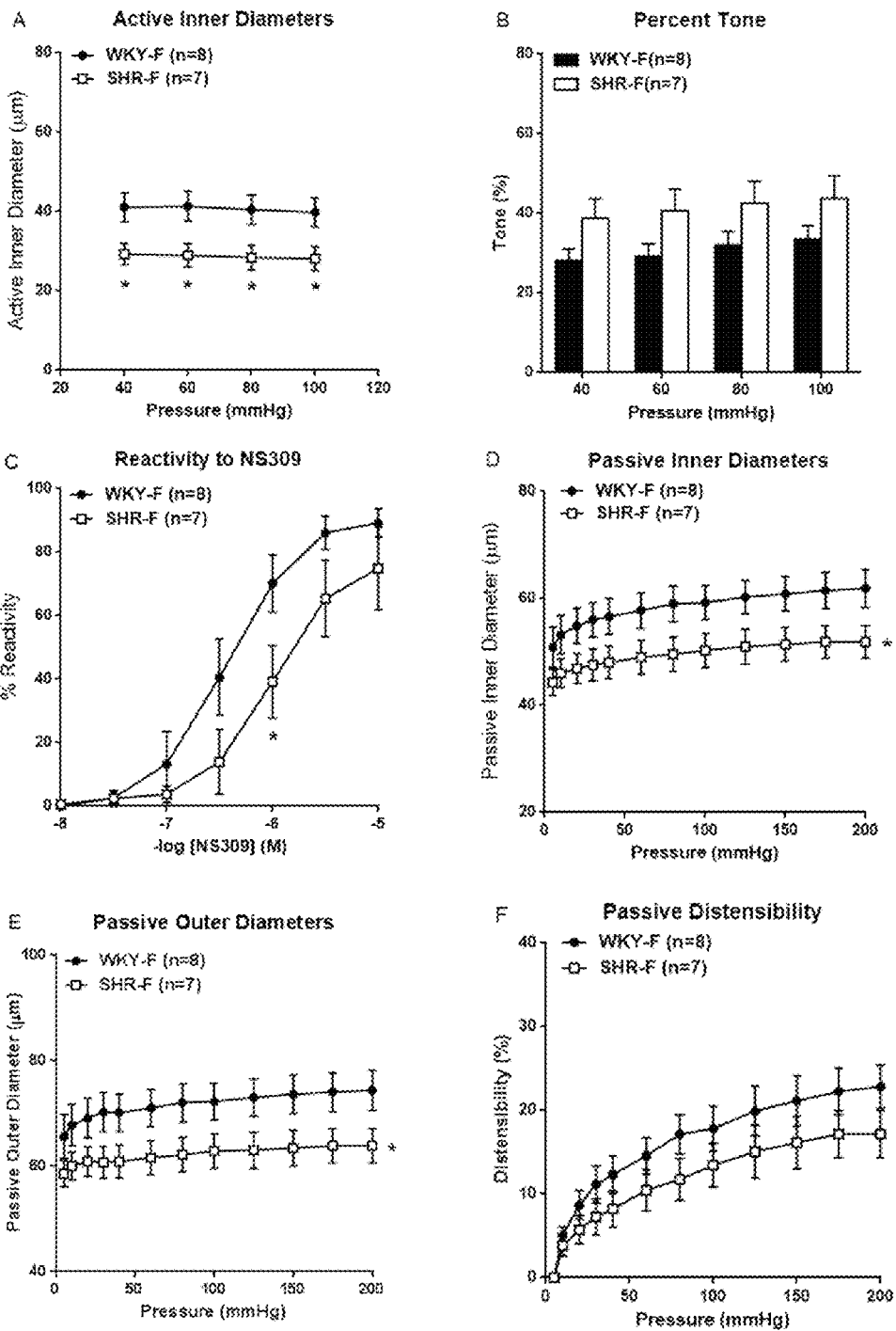
FIG. 4 is a set of graphs showing the effect of hypertension on the function and structure of PA. Graphs showing A) active ID, B) percent tone, C) reactivity to NS309, D) passive ID, E) passive OD, and F) passive distensibility of PA from WKY-F and SHR-F groups. Functionally, chronic hypertension decreased active inner diameters and decreased reactivity to the $SK_{Ca}/IK_{Ca}$ activator NS309. Structurally, chronic hypertension decreased passive ID, OD and increased distensibility. *p<0.05 versus WKY-F.

The effect of hypertension on myogenic activity and endothelial function of PA was determined herein. The SHR-F animals studied in these Examples are a model of chronic hypertension as they have substantially higher systolic, diastolic, and mean pressures. PA from SHR-F had smaller active inner diameters in response to increased pressures (FIG. 4A). Percent tone of PA was also increased in SHR-F, although this was not statistically significant (FIG. 4B). PA reactivity of NS309 was decreased in SHR-F group, as suggested by rightward shift of the concentration-response curve (FIG. 4C). However, constriction to L-NNA and reactivity to the NO donor SNP were similar in PA between WKY-F and SHR-F, suggesting NO-dependent vasodilation and smooth muscle responses to NO were not affected by hypertension (Suppl. FIG. 4A, 4B). These are the first results we are aware of showing significant vasoconstriction and endothelial dysfunction of PA during hypertension.

Hypertension-induced structural changes of cerebral penetrating vessels have been previously shown using histological methods. A limitation of histological approaches to study vessel structure is that biomechanical properties cannot be determined. Thus, to better understand structural changes, we assessed structural and biomechanical alternations of isolated vessels in response to changes in pressures. Passive ID and OD were significantly decreased in PA from SHR-F at all pressures tested (p<0.05), suggesting inward remodeling (FIG. 4D, 4E). However, WT was not changed in PA from SHR-F (FIG. 2C). Together, these results demonstrate that hypertension caused inward eutrophic remodeling of PA. Despite structural remodeling, distensibility was not significantly different in PA from SHR-F (FIG. 4F), although it was decreased at all pressures compared to WKY-F. Inward eutrophic remodeling of PA during hypertension was distinctly different from that of MCA. Chronic hypertension caused decreased ID (FIG. 2A) and increased WT (FIG. 2B) with decreased distensibility (FIG. 2C) in MCA. Thus, chronic hypertension causes differential structural remodeling in PA and MCA that may be an important consideration for cerebral SVD.

Example 9

Effects of Relaxin Treatment on MCA and PA During Chronic Hypertension

Figure 5:
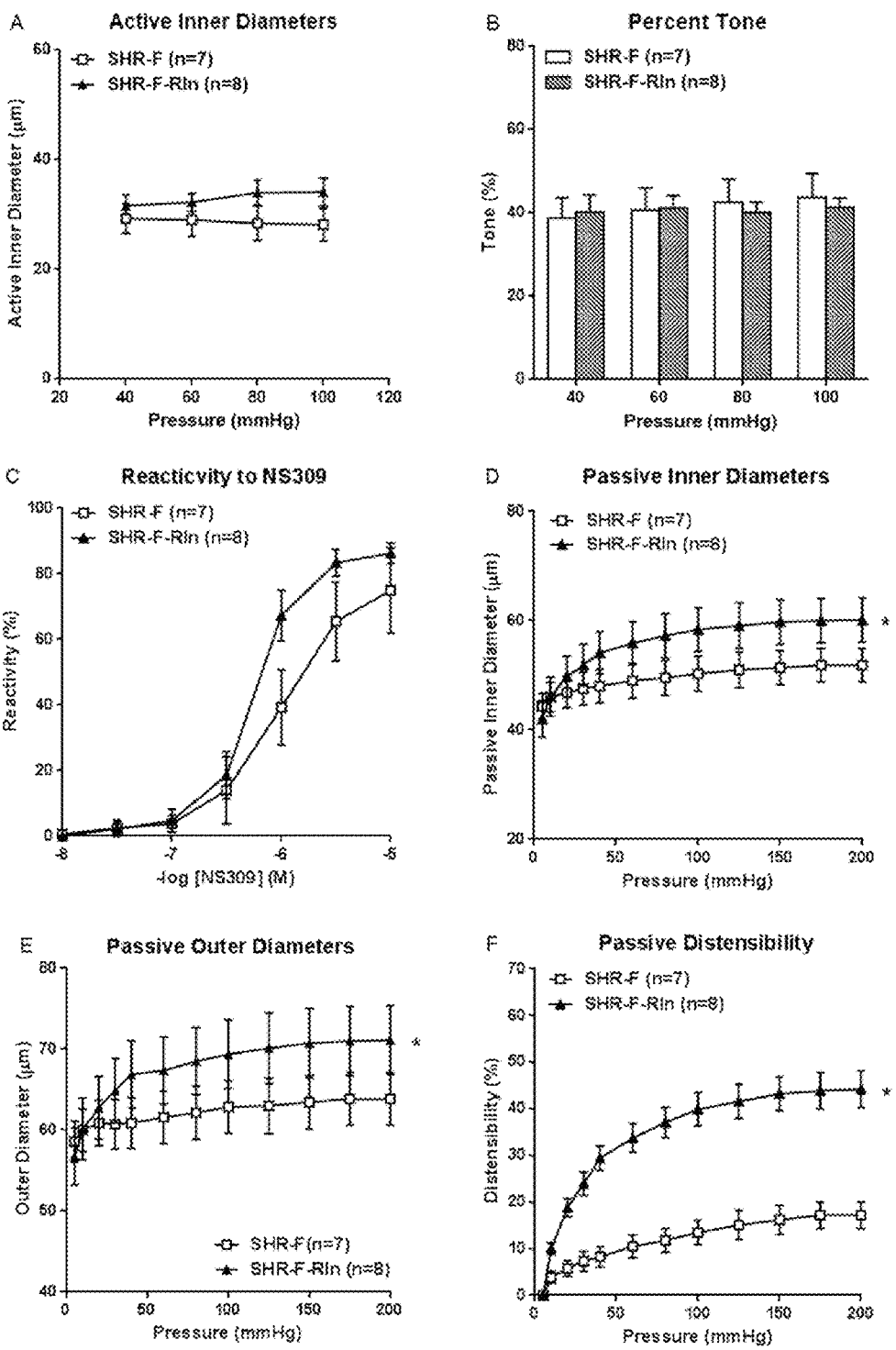
FIG. 5 is a set of graphs showing the effect of relaxin on hypertension-induced vascular changes of PA. Graphs showing A) active ID, B) percent tone, C) reactivity to NS309, D) passive ID, E) passive OD, and F) passive distensibility of PA from untreated SHR-F and SHR-F treated with relaxin (SHR-F—Rln). Relaxin increased reactivity to the $SK_{Ca}/IK_{Ca}$ activator NS309, increased passive ID, OD and distensibility without affecting myogenic tone of PA in hypertension. *p<0.05 versus SHR-F.

Our previous study showed that relaxin causes outward remodeling of PA in normotensive rats, leading us to hypothesize relaxin could potentially be a treatment for cerebral SVD during hypertension. SHR-F rats were treated with relaxin at 16 weeks of age and experimented on 18 weeks old, which matched the age of untreated SHR-F and WKY-F. Relaxin treatment increased circulating relaxin to the level of mid- to late-pregnancy (Table 1). Thus, circulating levels of relaxin were physiological in the treated animals. Relaxin treatment did not affect blood pressures of SHR-F. Despite previous findings in small renal arteries, relaxin treatment did not affect myogenic reactivity (FIG. 5A) or myogenic tone (FIG. 5B) of PA when compared to untreated SHR-F. Relaxin tended to increase reactivity to NS309 (inner diameter increased by 67±8 vs. 39±11% in SHR-F at $10^{-6}$ M; p=0.058), suggesting relaxin may increase endothelium-derived hyperpolarizing factor (EDHF)-dependent vasodilation of PA (FIG. 5C). Structurally, relaxin increased passive ID (FIG. 5D) and OD (FIG. 5E), demonstrating relaxin enlarged PA in SHR-F. The structural enlargement of PA was largely due to relaxin-induced increased distensibility (FIG. 5E) rather than true remodeling (ID 42±3 vs. 44±2 μm in SHR-F at 5 mmHg) (FIG. 5D). The effect of relaxin on upstream MCA from the same animals was different from that of PA. Relaxin had no effect on the structure of MCA, with passive ID (FIG. 2A), WT (FIG. 2B), and distensibility (FIG. 2C) of MCA unaffected. Interestingly, the effect of relaxin on PA structure in SHR was different from what we previously reported on normotensive rats. Relaxin caused outward hypertrophic remodeling without affecting distensibility in PA from normotensive rats while it caused outward eutrophic remodeling with increased distensibility in hypertensive rats.

Example 10

Expression of Relaxin Receptors in MCA and PA

TABLE 1

Relaxin concentration in serum and cerebrospinal fluid (CSF) from all groups of animals.

| Groups | Serum (ng/ml) | CSF (ng/ml) |
|---|---|---|
| SHR-F (n = 7) | −0.8 ± 0.2 | — |
| SHR-F-Rln (n = 8) | 93 ± 11 | — |

TABLE 1-continued

Relaxin concentration in serum and cerebrospinal fluid (CSF) from all groups of animals.

| Groups | Serum (ng/ml) | CSF (ng/ml) |
|---|---|---|
| SHR-F-Rln-Axi (n = 8) | 114 ± 19 | — |
| SHR-F-Rln-CSF (n = 4) | 38 ± 5 | 0.11 ± 0.03 |

The results above showed that relaxin selectively reverses inward remodeling by increasing distensibility of PA, but not MCA. We therefore investigated the underlying mechanisms of relaxins selectivity for brain PA. One hypothesis for the differential effect of relaxin on PA versus MCA is that there is differential expression of the primary relaxin receptor, RXFP1, on these vessels. In a qPCR experiment comparing RXFP1 mRNA expression in MCA, PA, and brain cortex, there was no expression after 40 cycles in MCA and PA and low expression in brain cortex when compared to the housekeeping gene β-actin (Table 2). To confirm RXFP1 was not expressed in PA and MCA, RNA was amplified to increase input of cDNA to the qPCR reaction. After amplification, we still found no expression of RXFP1 in PA and MCA (Table 2). We also determined expression of another relaxin receptor RXFP2 in PA and MCA because relaxin can also bind RXFP2. We found that RXFP2 was also not expressed in PA in amplified samples and only 1 sample had expression of RXFP2 in MCA. These results were not due to low cDNA input to the qPCR reaction because cDNA input was increased by 1000 fold in amplified samples. Thus, despite a significant effect of relaxin on PA, these results suggest that the selective effect of relaxin on PA is not due to greater expression of relaxin receptors.

TABLE 3

Threshold cycles (Ct) of qPCR for relaxin family peptide receptors 1 and 2 (RXFP1 and 2) and β-actin (housekeeping) in middle cerebral arteries (MCA), parenchymal arterioles (PA), and brain cortex from untreated female SHR.

| | Unamplified | | | Amplified | |
|---|---|---|---|---|---|
| | MCA | PA | Brain Cortex | MCA | PA |
| B-actin | 27.83 | 28.16 | 27.25 | 16.99 ± 0.15 | 17.48 ± 0.55 |
| RXFP1 | Undet. | Undet. | 36.00 | Undet. | Undet. |
| RXFP2 | — | — | — | 33.84 | Undet. |

Example 11

Determination of Relaxin Levels in CSF

One major difference between MCA and PA is that PA are closely associated with other cell types in the brain such as neurons that are known to express RXFP1 whereas MCA lie on top of the brain in the subarachnoid space. Thus, it is possible that relaxin is acting on PA through an interaction with other cells within the brain tissue that express RXFP1. However, relaxin must cross the BBB for this to be correct. Therefore, we measured relaxin levels in CSF after systemic treatment for 2 weeks and found that human relaxin was present in CSF, about 0.3% of that in the circulation (Table 1). This is the first direct evidence showing that systemic administration of human relaxin crosses the BBB and may underlie the mechanism by which relaxin selectively affects PA.

Example 12

The Role of VEGF on Structural Remodeling of PA

Because relaxin is able to cross the BBB and RXFP1 is expressed in cells within the brain cortex such as neurons that are closely associated with PA, we hypothesized that relaxin acts to selectively remodel PA through interaction with the brain tissue. In this manner, the effect of relaxin would be selective because there is no cell type known to express RXFP1 close to MCA that lie within the subarachnoid space. One target of relaxin that could promote remodeling of PA is VEGF. We determined expression of VEGF in brain cortex comparing relaxin-treated SHR-F with untreated WKY-F and SHR-F using qPCR and immunohistochemistry. Representative photomicrographs of VEGF staining in brain cortex from different groups of animals are shown in FIG. 6A. Relaxin treatment significantly increased VEGF staining when compared to untreated SHR-F (Graph, FIG. 6A). This result was confirmed by using Photoshop to analyze the grayscale histogram of the photomicrographs. PCR analysis of mRNA expression also showed that relaxin increased VEGF mRNA expression in brain cortex (FIG. 6B).

Figure 7:
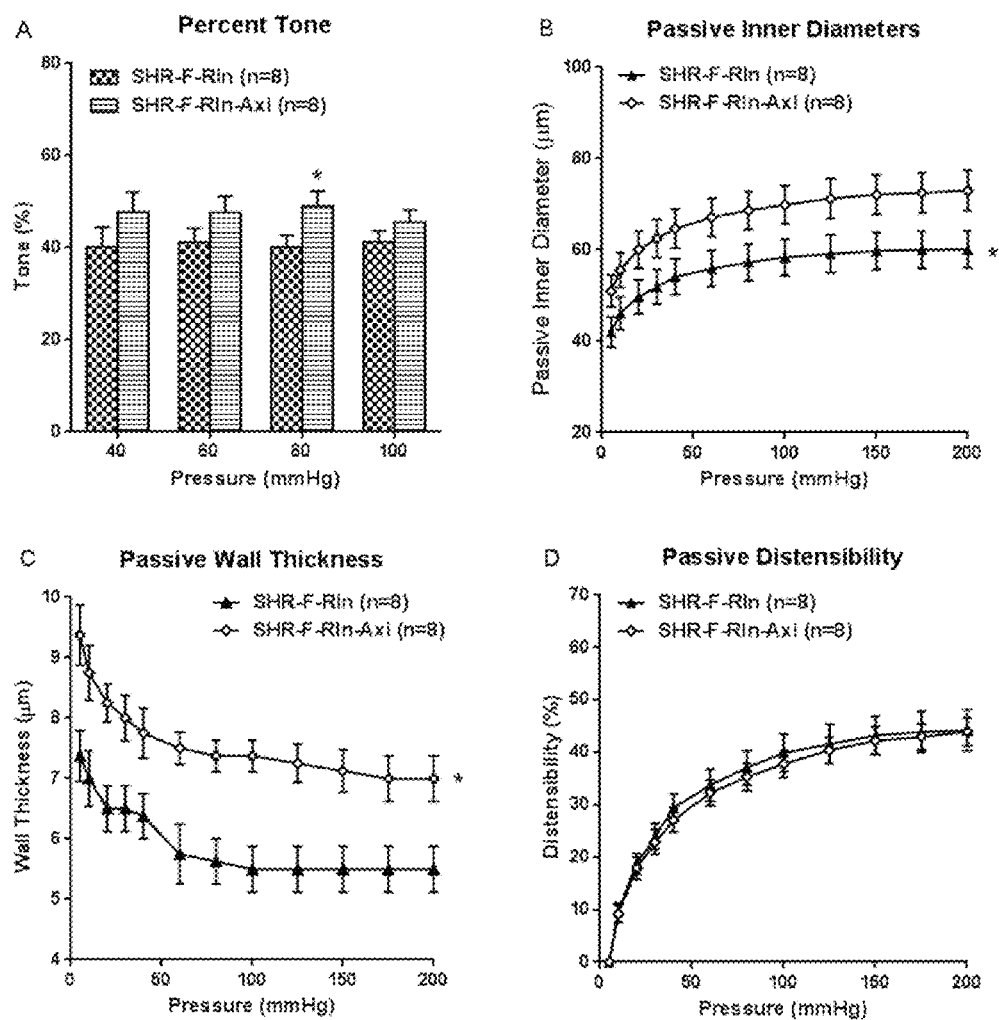
FIG. 7 is a set of graphs showing the effect of VEGF-R tyrosine kinase inhibition with axitinib on relaxin-mediated remodeling in PA during hypertension. Graphs showing A) percent tone, B) passive ID, C) passive WT, and D) passive distensibility of PA comparing SHR-F-Rln and SHR-F co-treated with relaxin and axitinib (SHR-F-Rln-Axi). Axitinib and relaxin co-treatment significantly increased tone of PA when compared to relaxin alone. Structurally, axitinib plus relaxin increased passive ID and WT of PA compared to relaxin only. Despite these structure changes, axitinib plus relaxin did not affect relaxin-induced increased distensibility. *p<0.05 vs. SHR-F-Rln.

As relaxin increased VEGF expression in the brain cortex, we determined the effect of VEGF-R inhibition and investigated the role of VEGF in relaxin-mediated remodeling of PA in SHR-F. Age and body weight of SHR-F-Rln-Axi animals were similar to that of relaxin-treated SHR-F. Circulating relaxin levels in SHR-F-Rln-Axi group of animals were similar to that of relaxin-treated SHR-F (Table 1). VEGF-R inhibition with axitinib did not alter blood pressure. Axitinib co-treated with relaxin increased myogenic tone compared to SHR-F-Rln group (FIG. 7A). Structurally, axitinib plus relaxin significantly increased ID (FIG. 7B) and WT of PA compared to SHR-F-Rln group (FIG. 7C). Despite these structural changes, axitinib plus relaxin did not affect distensibility of PA (FIG. 7D). These results suggest that inhibition of VEGF signaling in SHR with relaxin treatment caused outward remodeling. Thus, increased VEGF appears to prevent outward remodeling and hypertrophy in response to relaxin without affecting distensibility.

Example 13

The Role of PPARγ on Vascular Remodeling of PA

Figure 8:
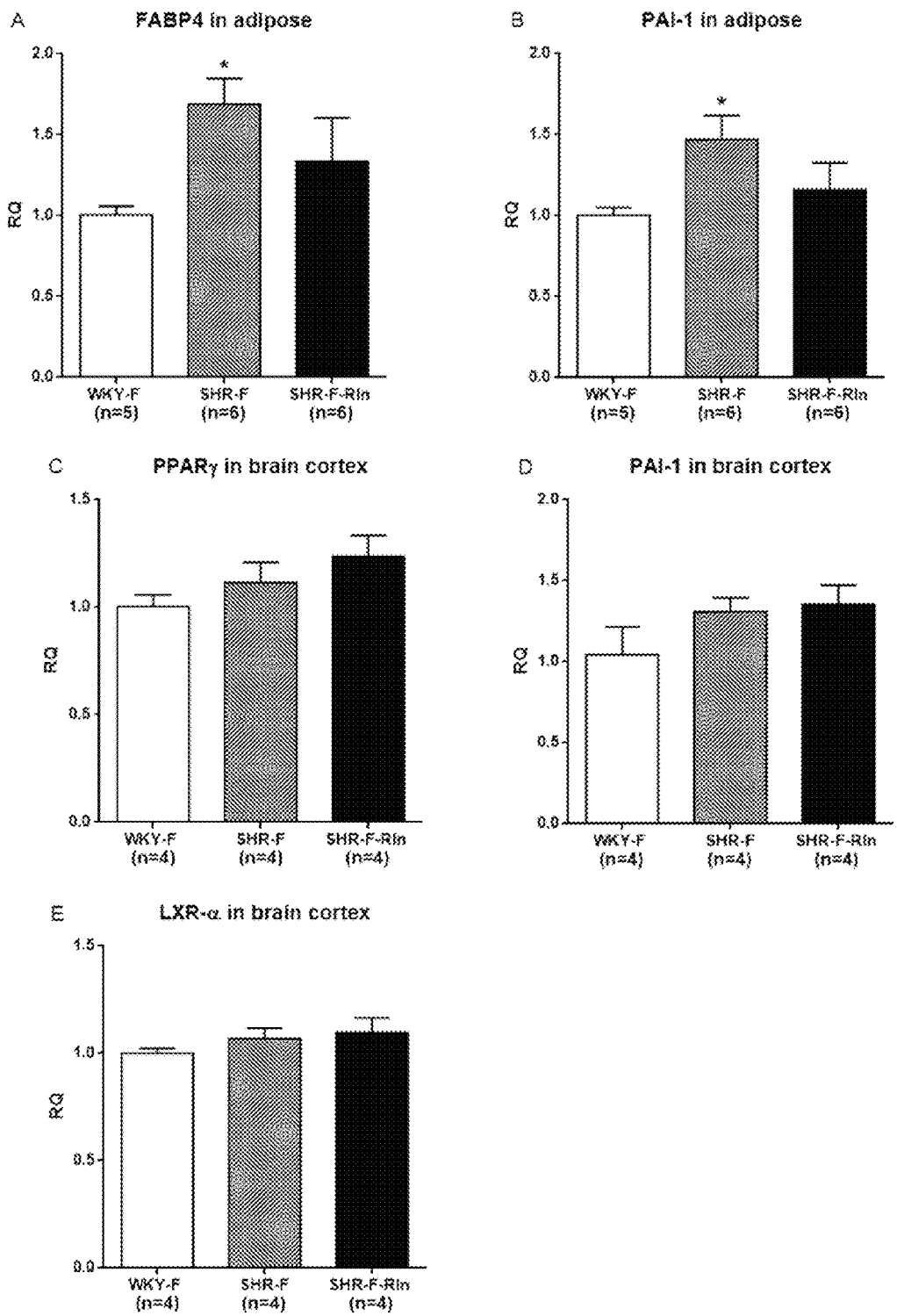
FIG. 8 is a set of graphs showing the effect of relaxin on expression of PPARγ and PPARγ target genes in adipose tissue and brain cortex during hypertension. Graphs showing expression of A) FABP4 in adipose, B) PAI-1 in adipose, C) PPARγ in brain cortex, D) PAI-1 in brain cortex, and E) LXR-α in brain cortex from WKY-F, SHR-F, and SHR-F-Rln groups. Expression of FABP4 and PAI-1 in adipose was significantly increased in SHR-F compared to WKY-F. Relaxin decreased expression of FABP4 and PAI-1 in adipose tissue, although this was not statistically significant. Relaxin did not affect expressions of PPARγ and its target genes in brain cortex. *p<0.05 versus WKY-F.

Relaxin causes outward remodeling in PA through activation of PPARγ in normotensive rats. Therefore, we determined if expression of PPARγ and its target genes were altered after relaxin treatment in brain cortex from hypertensive rats. We also determined PPARγ target gene expression in adipose tissue after relaxin treatment, where PPARγ is highly expressed. Expression on PPARγ target genes FABP4 and PAI-1 in adipose tissue were increased in SHR-F group (FIG. 8A, 8B). Relaxin decreased both FABP4 and PAI-1 expressions in adipose tissue, although this was not statistically significant. In brain cortex, expression of PPARγ, PPARγ target genes LXR-α and PAI-1 were similar among groups (FIG. 8C, 8D, 8E).

Discussion

The work described herein provides the first evidence that relaxin activates PPARγ in vivo, suggesting relaxin may be another endogenous activator of PPARγ. PPARγ activation appears to be involved in the underlying mechanism by which relaxin caused outward remodeling of PA and increased brain capillary density, but not larger upstream arteries. It is also demonstrated for the first time that relaxin crosses the BBB and can have an effect on the brain. The induction of factors such as VEGF support the neuroprotective effects of relaxin and agonists thereof.

The major finding here is that treating NP rats with relaxin to serum levels of mid- to late-pregnancy caused outward remodeling in PA, but not in MCA, demonstrating that relaxin causes selective remodeling of the cerebral vasculature within the brain parenchyma. This selective outward remodeling by relaxin was inhibited by treatment with GW9662, suggesting that relaxin activates PPARγ to cause remodeling of PA. In addition, relaxin caused changes in PPARγ target gene expression that was prevented by GW9662 in adipose tissue, confirming that relaxin activates PPARγ in this tissue. Although relaxin caused structural remodeling in PA, relaxin did not significantly affect myogenic reactivity, tone, or endothelial function in these vessels. Thus, this is the first study demonstrating an effect of relaxin on structural remodeling in the cerebral circulation and that this effect is dependent on PPARγ activation.

We found that PPARγ activation was involved in relaxin-induced outward remodeling in PA, as suggested by the inhibitory effect of GW9662 on relaxin-induced outward remodeling. Activation of PPARγ was further confirmed by GW9662 treatment that prevented relaxin-induced changes in PPARγ target gene expression in adipose tissue, where PPARγ is highly expressed. To our knowledge, this report is the first to show relaxin activates PPARγ after in vivo relaxin treatment. This finding has physiological significance because PPARγ is involved in regulating vascular function and structure, as demonstrated in ours and other studies Beyer et al. (2008) *Hypertension* 51, 867-871; Cipolla et al. (2009) *Reprod Sci* 16, 91A; Cipolla et al. (2010) *FASEB J.* 24, 979.974; Halabi et al. (2008) *Cell Metab* 7, 215-226. Together, these findings suggest that the protective effects of relaxin may also be related to its ability to activate PPARγ.

In this study, we found that expression of CD36 was decreased by relaxin in adipose tissue. This effect was prevented by a selective PPARγ inhibitor GW9662. A similar trend was also observed in another PPARγ target gene LXR-α, although the results were not statistically significant. These results are contrary to a previous study that relaxin increased expression of CD36 and LXR-α in transfected HEK-293T cells, that was unaffected by GW9662 Baumbach et al. (2004) *Circ Res* 95, 822-829. These results suggest the effect of relaxin may be tissue-specific and may work through different mechanisms to affect PPARγ activity. Because GW9662 inhibits binding of PPARγ ligands, the mechanism of PPARγ activation in adipose tissue may be different from that of HEK-293T cells, which was through a non-ligand-binding mechanism. Moreover, the PPARγ target gene PAI-1 was not significantly changed in vascular segments regardless of relaxin or GW9662 treatment. This result is not surprising as RXFP1 expression was very low in MCA and undetectable in PA. Thus, if PPARγ acts through the relaxin receptor we would not see much effect in vascular tissue that have very low or undetectable RXFP1 expression. These results also suggest that PPARγ-dependent selective outward remodeling of PA may not be a direct effect of relaxin that involves activation of RXFP1 in the vasculature. One possibility is that PPARγ is activated in astrocytes and/or neurons in response to relaxin treatment, and exerting a paracrine effect to the closely associated PA. As astrocytes are not present around pial arteries such as the MCA, this paracrine effect may explain the PPARγ-dependent selective remodeling of PA.

Because relaxin did not affect the structure of MCA, overall cerebral vascular resistance is likely to be unchanged. However, as PA contributes to local vascular resistance and thus perfusion to downstream microcirculation, increased inner diameter may decrease local vascular resistance and hence increase blood flow locally that may be important for changes in local brain perfusion and metabolism. The selective effect of relaxin to increase brain capillary number may also aid in increasing perfusion and treat SVD of the brain, including leukoaraiosis, vascular dementia and Alzheimer's disease.

We have also shown that PPARγ activation during hypertension reversed capillary rarefaction and protected against increased BBB permeability. Because relaxin activated PPARγ it is likely that relaxin will be useful in treating conditions associated with increased BBB permeability including migraine, stroke, dementia, Alzheimer's disease, CADASIL, epilepsy and the neurological symptoms of preeclampsia and eclampsia.

Despite hypertension being an important risk factor for cerebral SVD, the impact of hypertension on PA remains largely unknown. We have shown that hypertension for 8 weeks caused EDHF-dependent endothelial dysfunction and increased myogenic tone, without affecting the NO-dependent vasodilator pathway. Moreover, chronic hypertension reduced lumen diameters of PA, consistent with histological findings in cerebral SVD patients. Inward remodeling reduces maximum vasodilation and vasodilator reserve of PA that further promotes ischemia during reductions of blood pressure. However, hypertension did not affect WT and distensibility of PA. Importantly, the impact of hypertension on PA appears to be unique from the upstream MCA, which was found to be outward hypertrophic remodeling with decreased distensibility. Thus, studying PA during hypertension in addition to pial vessels is essential for understanding of cerebral SVD.

This study shows for the first time that relaxin caused outward remodeling of PA during hypertension largely due to increased distensibility. PA with increased distensibility may have improved vasodilator reserve and better normalization to increased pulse pressure during hypertension. Increased pulse pressure is a major determinant of vascular hypertrophy, which contributes to changes in stiffness of the wall. In addition, relaxin tended to improve EDHF-dependent vasodilation of PA during hypertension. Relaxin therefore may have two beneficial effects. First, relaxin-mediated increased distensibility may reduce the impact of increased pulse pressure and enhanced vasodilator reserve. Second, relaxin-induced enhanced EDHF-dependent vasodilation in PA could be a compensatory mechanism for vasodilation in disease state, such as stroke when NO-dependent vasodilation is compromised. Together, these effects of relaxin could decrease vascular resistance of PA and prevent hypertension-induced hypoperfusion.

Figure 9:
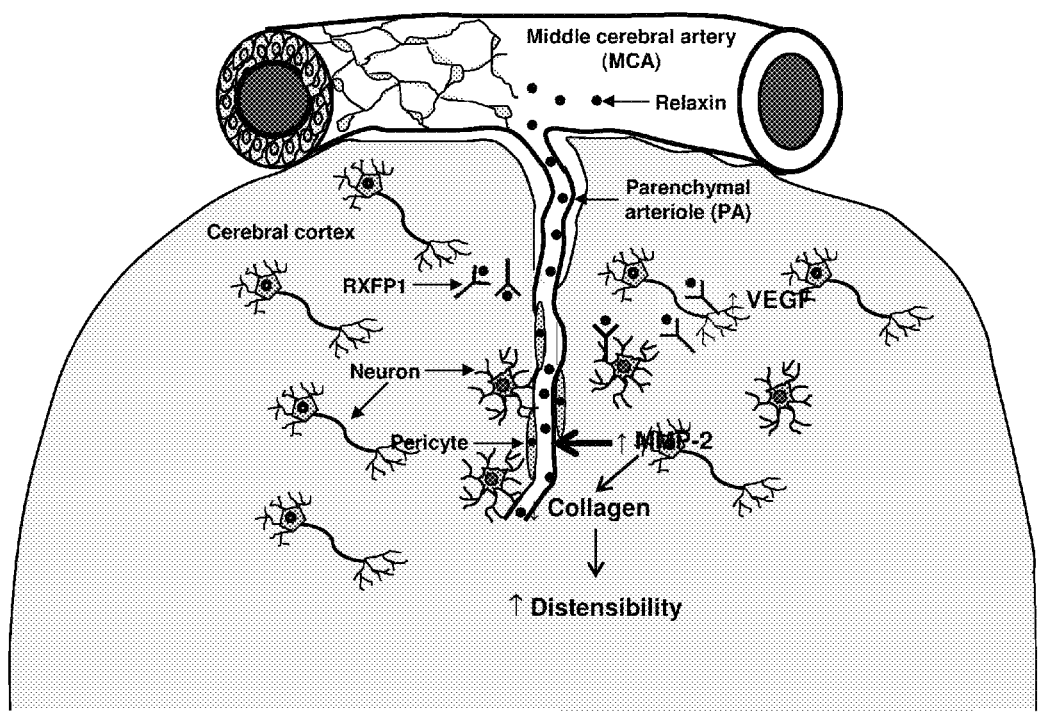
FIG. 9 is a diagram showing the proposed mechanism for selective effects of relaxin on PA during hypertension. RXFP1 and RXFP2 are not expression on cerebral vasculature. However, systemic administration of human relaxin-2 crosses the blood-brain barrier, thus gaining access to other cells in the brain cortex that express RXFP1, such as neurons. Relaxin activates RXFP1 in cells within the brain cortex and up-regulates VEGF and MMP-2 that are available to interact with the vasculature within the brain parenchyma. Activated MMP-2 in brain cortex may increase PA distensibility by reducing collagen in PA wall. The effect of relaxin is selective on PA because there is no other cell type that is known to expresses RXFP1 associated with MCA that are located within the subarachnoid space.

Relaxin interacts with RXFP1 to exert its effects in small renal and systemic arteries. However, this does not appear to be the case in PA because RXFP1 and RXFP2 are not expressed in PA. Because RXFP1 is expressed in neurons Gundlach et al. (2009) *Ann N Y Acad Sci* 1160, 226-235, relaxin may activate RXFP1 in neurons (or other cell types in the brain cortex) and exerts its effects through a paracrine manner on PA. The first evidence we found to support this hypothesis was that relaxin crosses the BBB. Because human relaxin is not made in rat brains, only systemically administered human relaxin was detected in CSF. Also, a human relaxin-specific ELISA was used further suggesting only systemically administered human relaxin was detected in rat brain. This is the first direct evidence to show circulating relaxin crosses the BBB (FIG. 9). It is unknown how relaxin passes through the BBB. We speculate that relaxin could not freely pass through tight junctions because of its large 6 kD size. However, it is possible that relaxin crosses the BBB through a receptor-mediated transport similar to that of insulin, a similar protein hormone.

Relaxin may be acting in a paracrine manner on PA through increased VEGF in neurons. VEGF is involved in processes of vascular remodeling, including cell proliferation and migration Cipolla et al. (2009) *Stroke* 40, 1451-1457. Moreover, VEGF has been shown to enhance MMP-mediated smooth muscle migration, underlying the interaction between VEGF and MMP in vascular remodeling. Livak et al. (2001) *Methods* 25, 402-408. The finding that VEGF expression was increased in brain cortex by relaxin led us to investigate the role of VEGF-R signaling inhibition on PA remodeling during hypertension. Interestingly, although VEGF-R inhibition did not appear to affect the increased distensibility of PA by relaxin, relaxin plus axitinib caused hypertrophic outward remodeling of PA. Because VEGF is known to increase production of NO by up-regulating endothelial NOS, it is possible that when VEGF is inhibited, NO production is reduced, preventing inhibition of smooth muscle growth. This increased smooth muscle growth could cause hypertrophic outward remodeling of PA as seen in this study when VEGF signaling is inhibited in the presence of relaxin.

Relaxin-induced VEGF expression appears to be selective for remodeling of PA but not distensibility. Relaxin may increase distensibility of PA by direct up-regulation of MMP-2 and/or MMP-9. MMP-2 expression was only increased by relaxin in brain cortex but not PA. This compartmental difference in MMP-2 expression supports the concept that there is an interaction between brain cortex MMP-2 and PA. The cell type(s) that are involved in this process within the brain cortex is unknown, but may involve neurons where RXFP1 and RXFP2 are known to express. MMP-2 is known to digest vascular wall collagen IV. Thus, increased MMP-2 expression in other cell types within the brain cortex may reduce PA wall collagen IV, leading to decreased collagen-to-elastin ratio, and hence increased distensibility (FIG. 9).

The effect of relaxin on PA was distinctly different in normotensive and hypertensive conditions. Similar treatment of relaxin caused outward hypertrophic remodeling in PA without affecting distensibility in normotensive rats, while it caused outward eutrophic remodeling of PA in hypertensive rats largely due to increased distensibility. In addition, PPARγ is involved in relaxin-mediated remodeling of PA in normotensive rats. PPARγ target genes remained unchanged within the brain and cerebral vasculature in response to relaxin. However, in adipose tissue where PPARγ is highly expressed, PPARγ target genes were significantly affected by relaxin only in the normotensive rats. The lack of significant activation of PPARγ by relaxin in hypertensive rats may be due to mutation of PPARγ co-activator-1 (PGC-1) and that may be one reason there is differential remodeling of PA by relaxin between hypertensive and normotensive rats. Interestingly, relaxin-mediated remodeling of PA in SHR was similar to that of normotensive rats with VEGF-R signaling inhibition. This similarity may be explained by the interaction of PPARγ and VEGF. It has been reported that PPARγ agonists inhibit VEGF in endothelial cells. Desouza et al. (2009) *Vascular pharmacology* 51, 162-168. If this is the case, relaxin-induced PPARγ activation in normotensive rats could inhibit VEGF, which could be similar to relaxin and axitinib co-treatment in hypertensive rats, resulting similar PA remodeling.

In the present study, we used young SHR that were hypertensive for 10 weeks. Despite smaller and more constricted PA compared to normotensive animals, cerebral blood flow is similar compared to age-matched WKY. Therefore, it is likely that clinical features of cerebral SVD have not been developed at this age of SHR. However, this study provides evidence that hypertension impacts PA function and structure that can progress to hypoperfusion and white matter damage occurs early in the disease process. Importantly, early intervention to treat cerebral SVD may also be important to prevent cognitive decline later in life.

In summary, hypertension caused endothelial dysfunction and inward remodeling of PA. Long-term effect of these vascular changes could lead to chronic hypoperfusion and white matter damage that are observed in cerebral SVD. Relaxin treatment reversed hypertension-induced inward remodeling of PA, largely due to increased distensibility. Relaxin appears to cross the BBB and gain access to the brain cortex, an effect that may up-regulate VEGF and MMP-2 to increase distensibility of PA (FIG. 9). Relaxin-induced increased distensibility of PA during chronic hypertension may improve vasodilator reserve that can potentially prevent hypoperfusion.

List of Nonstandard Abbreviations

CSF: cerebrospinal fluid; EDHF: endothelium-derived hyperpolarizing factor; EGTA: ethyleneglycoltetraacetic acid; ELISA: enzyme-linked immunosorbent essay; FABP4: fatty acid-binding protein; ID: inner diameter; IKCa: intermediate-conductance calcium-activated potassium channels; L-NNA: L-nitro-n-arginine; LXR-α: liver X receptor-alpha; HRP: horseradish peroxidase; MCA: middle cerebral arteries; MMP: matrix metalloproteinase; NO: nitric oxide; NOS: nitric oxide synthase; OD: outer diameter; PA: parenchymal arterioles; PAI-1: plasminogen activator inhibitor-1; PBS: phosphate buffered saline; PCR: polymerase chain reaction; PGC-1: peroxisome proliferator-activated receptor-gamma co-activator-1; PPARγ: peroxisome proliferator-activated receptor-gamma; PSS: physiological salt solution; RXFP: relaxin family peptide receptor; SHR: spontaneous hypertensive rats; SKCa: small-conductance calcium-activated potassium channels; SNP: sodium nitroprusside; SVD: small vessel disease; WKY: Wistar-Kyoto; WT: wall thickness; VEGF: vascular endothelial growth factor.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating a small vessel disease of the brain, comprising
identifying a subject as having a small vessel disease of the brain and chronically administering to the subject having the small vessel disease of the brain a relaxin or agonist thereof, wherein the subject is not otherwise in need of treatment with relaxin or agonist thereof in an effective amount to promote outward remodeling of the small vessels of the brain, wherein the small vessel disease of the brain is due to hypertension and wherein the relaxin or agonist thereof crosses the blood brain barrier.

2. The method of claim 1, wherein the subject has CADASIL (cerebral autosomal dominant arteriopathy with subcortical infarcts and leukoencephalopathy).

3. The method of claim 1, wherein the relaxin or agonist thereof is recombinant human relaxin.

4. The method of claim 1, further comprising administering to the subject a PPAR-γ agonist.

5. The method of claim 4, wherein the PPAR-γ agonist is a thiazolidinedione.

6. The method of claim 1, wherein the relaxin or agonist thereof is administered to the subject orally.

7. The method of claim 1, wherein the relaxin or agonist thereof is administered to the subject transdermally.

8. The method of claim 1, wherein the relaxin or agonist thereof is administered to the subject subcutaneously.

9. The method of claim 1, wherein the relaxin or agonist thereof is administered to the subject in a sustained release formulation.

10. The method of claim 1, wherein the relaxin is administered to the subject at a predetermined rate so as to maintain a serum concentration of at least about 1 ng/ml.

11. A method for treating a small vessel disease of the brain, comprising
identifying a subject as having small vessel disease of the brain and administering to the subject a relaxin or agonist thereof, wherein the small vessel disease of the brain is due to hypertension and wherein the relaxin or agonist thereof crosses the blood brain barrier.

12. A method for treating a disease of the brain, comprising
identifying a subject as having a small vessel disease of the brain due to hypertension and administering to the subject a relaxin or agonist thereof, wherein the relaxin or agonist thereof has a neuroprotective effect in the brain.

* * * * *